(12) United States Patent
Vahlne

(10) Patent No.: US 6,258,932 B1
(45) Date of Patent: Jul. 10, 2001

(54) PEPTIDES THAT BLOCK VIRAL INFECTIVITY AND METHODS OF USE THEREOF

(75) Inventor: Anders Vahlne, Hovås (SE)

(73) Assignee: Tripep AB (BE)

( * ) Notice: Subject to any disclaimer, the term of this patent is extended or adjusted under 35 U.S.C. 154(b) by 0 days.

(21) Appl. No.: 09/370,368

(22) Filed: Aug. 9, 1999

(51) Int. Cl.$^7$ .................................................. A61K 38/06
(52) U.S. Cl. ........................ 530/331; 435/5; 435/235.1; 514/2; 514/18; 530/300
(58) Field of Search .................. 435/5, 235.1; 530/300, 530/331; 514/2, 18

(56) References Cited

U.S. PATENT DOCUMENTS

| | | |
|---|---|---|
| 4,612,337 | 9/1986 | Fox et al. . |
| 4,818,540 | 4/1989 | Chinen et al. . |
| 5,627,035 | 5/1997 | Vahlne et al. . |
| 5,843,995 | 12/1998 | Rana et al. . |

FOREIGN PATENT DOCUMENTS

| | | |
|---|---|---|
| 0 421 074 | 4/1991 | (EP) . |
| WO90/04390 | 5/1990 | (WO) . |
| WO 92/20795 | 11/1992 | (WO) . |
| WO 98/09985 | 3/1998 | (WO) . |
| WO 99/09056 | 2/1999 | (WO) . |

OTHER PUBLICATIONS

Lassila, et al., "A Role for Lys–His–Gly–NH$_2$ in Avian and Murine B Cell Development," *Cell. Immun.*, 122:319–328 (1989).

*Nature*, Martin, 345:572–573 (1990), "Fast–acting slow viruses".

*FEBS Lett.*, Richards, 253:214–216 (1989) "Inhibition of the aspartic proteinase from HIV–2".

*J. Exp. Med.*, Grannelli–Piperno, et al., 184:2433–2438 (1996) "Efficient Interaction of HIV–1 with Purified Dendritic Cells via multiple chemokine Coreceptors".

*Science*, Hwang, et al., 253:71–74 (1991) "Identification of the envelope V3 loop as the primary determinant of cell tropism in HIV–1".

*Science*, Kowalski, et al., 237:1351–1355 (1987) "Functional regions of the envelope glycoprotein of human immunodeficiency virus type I".

*Science*, Gamble, et al., 278:849 (1997) "Structure of the carboxyl–terminal dimerization domain of the HIV–1 capsid protein".

*Appl. Microbiology*, Miller, et al., 16:1489 (1968) "Antiviral activity of carbobenzoxy Di– and Tripeptides on measles virus".

*Virology*, Fields ed. Third edition, Lippencott–Raven pub., (1996), pp. 62, 70, 1513, 1645–46, 1778, 1882–83, 1886–89, 2047, 2113, 2221, 2717.

Bachem Catalog, Bachem Bioscience Inc. 1993, pp. 28, 29, 34, 145, 267, 332, 333, 457, 535, 536, 541, 546 and 553.*

Louis et al. Hydrophilic peptides derived from the transframe region of Ga–Pol inhibit the HIV–1 protease. Biochemistry. 1998, vol. 37, pp. 2105–2110.*

Henderson et al. ; Gag proteins of the highly replicative MN strain of human immunodeficiency virus type 1: postranslational modifications, proteolytic processing, and complete amino acid sequences. Journal of Virology vol. 66 (1992), p 1856–1865.*

Niedrig et al.; Inhibition of infectious human immunodeficiency virus type 1 particle formation by Gag protein derived peptides. Journal of General Virology. vol. 75 (1994), p. 1469–1474.*

Sigma, Peptide and Amino Acid Catalog. 1995–96, p.27 and p.70.*

Sheppard R.C.; Peptide synthesis, solid phase. In: Molecular Biology and Biotechnology:a comprehensive desk reference. Ed: Meyers R.A. 1995, VCH Publishers Inc., New York, NY.*

* cited by examiner

*Primary Examiner*—Jeffrey Stucker
*Assistant Examiner*—Ulrike Winkler
(74) *Attorney, Agent, or Firm*—Knobbe, Martens, Olson & Bear, LLP

(57) ABSTRACT

The discovery of peptides in amide form that inhibit viral infection, including human immunodeficiency virus (HIV) infection is disclosed. Methods of use of peptides are also disclosed including use in medicaments for the treatment and prevention of viral infection, such as HIV infection.

33 Claims, 10 Drawing Sheets

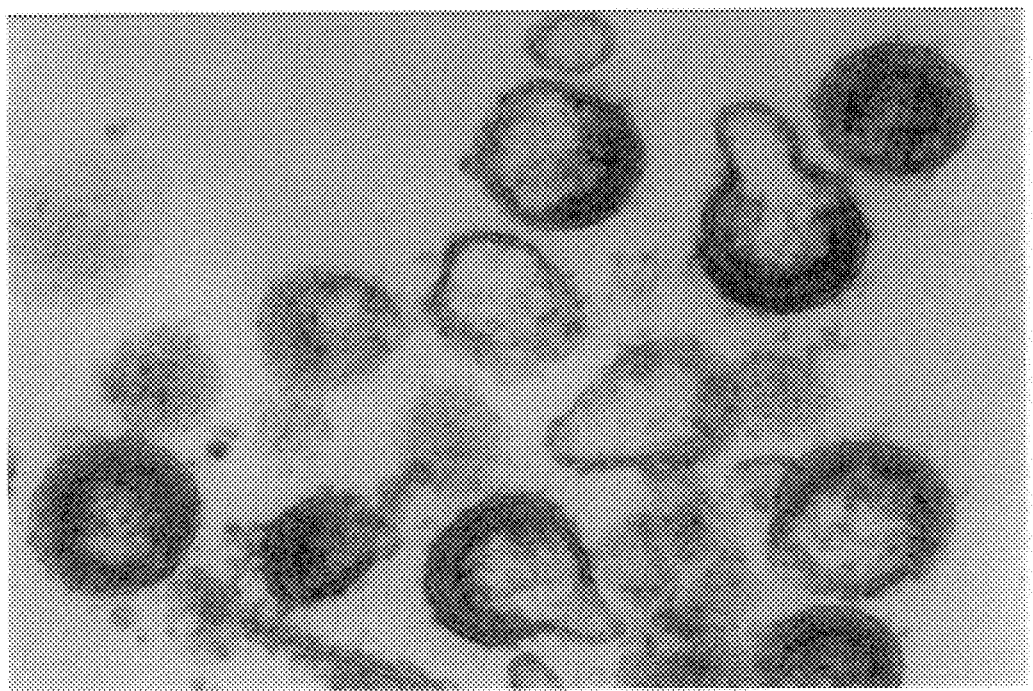
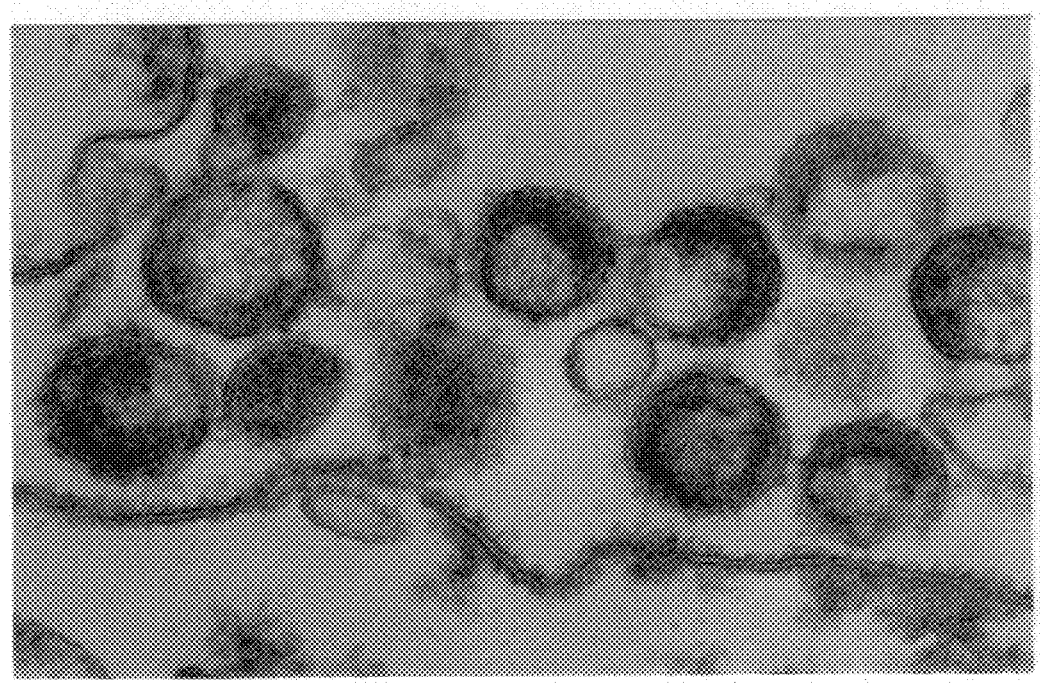
FIG.3

| | | |
|---|---|---|
| HIV-1 | SPTS-ILDIKQGPKEPFRDYVDRFYKTLRAEQA----SQEVKNWMTETLLVQNANPDCKTILKALG-PAATLE-EMMTAC---QGVGGPGHK--ARVL// | (SEQ. ID NO. 3) |
| HIV-2 | NPTN-ILDIKQGPKEPFQSYVDRFYKSLRAEQT----DPAVKNWMTQTLLIQNANPDCKLVLKGLG-MNPTLEEMLTAC---QGVGGPGQK--ARLM// | (SEQ. ID NO 4) |
| SIV | NPVN-ILDIKQGPKEPFQSYVDRFYKSLRAEQA----DPAVKNWMTQTPLIQNANP DCKLVLKGLG-MNPTLEEMLTAC---QGVGGPGQK--ARLM// | (SEQ. ID NO. 5) |
| HTLV-1 | DPS--WASILQGLEEPYHAFVERLNIALDNGLP----EGTPKDPILRSLAYSNANKECQKLLQARG--HTNSPLGDMLR AC---Q-TWTPKDK--TKVL--// | (SEQ. ID NO. 6) |
| MPMV | DPGASLTGVKQGPDEPFADFVHRLITTAGRIFG----SAEAGVDYVKQLAYENANPACQAAIRPYR--KKTDLTGYI LC--SDIGPSYQQGLAMA---// | (SEQ. ID NO. 7) |
| MMTV | ----LAGLKQGNEESYETFISRLEEAVYRMMP--RGEGSDIL IKQLAWENAN SLCQDLIRPIR--KTGTIQDYI RAC--LDASPAV VQGMAY---// | (SEQ. ID NO. 8) |
| MMLV | TN LAKVKGITQGPNESPSAFLERLKEAYRRYTPYDPEDPGQETNVSMSFIWQSA-PDIGRKLERLEDLRNKTL-GDLVREA--ERIFNKRE--------// | (SEQ. ID NO. 9) |
| RSV | EPTDPWADIMQGPSESFVDFANRLIKAVEGSDL----P PSARAPVIIDCFRQKSQPDIQQLIRAAP--STLTTPGEIIKY VLDRQKTAPLTDQGIAAAM// | (SEQ. ID NO. 10) |

MHR

FIG.5

SEQUENCE LISTING

<160> NUMBER OF SEQ ID NOS: 10

<210> SEQ ID NO: 1
<211> LENGTH: 32
<212> TYPE: DNA
<213> ORGANISM: Artificial Sequence
<220> FEATURE:
<223> OTHER INFORMATION: Oligonucleotide

<400> SEQUENCE: 1
cgtatccaga ggagagcatt tgttacaata gg         32

<210> SEQ ID NO: 2
<211> LENGTH: 26
<212> TYPE: DNA
<213> ORGANISM: Artificial Sequence
<220> FEATURE:
<223> OTHER INFORMATION: Oligonucleotide

<400> SEQUENCE: 2
gtgccacctg tcgactaaga aaccat         26

<210> SEQ ID NO: 3
<211> LENGTH: 294
<212> TYPE: PRT
<213> ORGANISM: Human Immunodeficiency Virus Type 1

<400> SEQUENCE: 3

Asn Ser Ser Gln Val Ser Gln Asn Tyr Pro Ile Val Gln Asn Val Gln
 1               5                  10                  15

Gly Gln Met Val His Gln Ala Ile Ser Pro Arg Thr Leu Asn Ala Trp
            20                  25                  30

```
Val Lys Val Glu Glu Lys Ala Phe Ser Pro Glu Val Ile Pro Met
         35                  40                  45

Phe Ser Ala Leu Ser Glu Gly Ala Thr Pro Gln Asp Leu Asn Thr Met
 50                  55                  60

Leu Asn Thr Val Gly Gly His Gln Ala Ala Met Gln Met Leu Lys Glu
 65                  70                  75                  80

Thr Ile Asn Glu Glu Ala Ala Glu Trp Asp Arg Leu His Pro Val His
                 85                  90                  95

Ala Gly Pro Ile Ala Pro Gly Gln Met Arg Glu Pro Arg Gly Ser Asp
                100                 105                 110

Ile Ala Gly Thr Thr Ser Thr Leu Gln Glu Gln Ile Gly Trp Met Thr
            115                 120                 125

His Asn Pro Pro Ile Pro Val Gly Glu Ile Tyr Lys Arg Trp Ile Ile
    130                 135                 140

Leu Gly Leu Asn Lys Ile Val Arg Met Tyr Ser Pro Thr Ser Ile Leu
145                 150                 155                 160

Asp Ile Lys Gln Gly Pro Lys Glu Pro Phe Arg Asp Tyr Val Asp Arg
                165                 170                 175

Phe Tyr Lys Thr Leu Arg Ala Glu Gln Ala Ser Gln Glu Val Lys Asn
                180                 185                 190

Trp Met Thr Glu Thr Leu Leu Val Gln Asn Ala Asn Pro Asp Cys Lys
            195                 200                 205

Thr Ile Leu Lys Ala Leu Gly Pro Ala Ala Thr Leu Glu Glu Met Met
210                 215                 220

Thr Ala Cys Gln Gly Val Gly Gly Pro Gly His Lys Ala Arg Val Leu
225                 230                 235                 240

Ala Glu Ala Met Ser Gln Val Thr Asn Ser Ala Thr Ile Met Met Gln
                245                 250                 255

Lys Gly Asn Phe Arg Ser Gln Arg Lys Ile Val Lys Cys Phe Asn Cys
                260                 265                 270

Gly Arg Glu Gly His Ile Ala Lys Asn Cys Arg Ala Pro Arg Lys Lys
            275                 280                 285

Gly Cys Trp Lys Cys Gly
        290
```

<210> SEQ ID NO: 4
<211> LENGTH: 521
<212> TYPE: PRT
<213> ORGANISM: Human Immunodeficiency Virus Type 2

<400> SEQUENCE: 4

```
Met Gly Ala Arg Asn Ser Val Leu Arg Gly Lys Lys Ala Asp Glu Leu
 1               5                  10                  15

Glu Lys Val Arg Leu Arg Pro Gly Gly Lys Lys Lys Tyr Arg Leu Lys
             20                  25                  30

His Ile Val Trp Ala Ala Asn Glu Leu Asp Lys Phe Gly Leu Ala Glu
         35                  40                  45

Ser Leu Leu Glu Ser Lys Glu Gly Cys Gln Lys Ile Leu Arg Val Leu
 50                  55                  60

Asp Pro Leu Val Pro Thr Gly Ser Glu Asn Leu Lys Ser Leu Phe Asn
 65                  70                  75                  80

Thr Val Cys Val Ile Trp Cys Leu His Ala Glu Glu Lys Val Lys Asp
                 85                  90                  95

Thr Glu Glu Ala Lys Lys Leu Ala Gln Arg His Leu Val Ala Glu Thr
                100                 105                 110
```

```
Gly Thr Ala Glu Lys Met Pro Asn Thr Ser Arg Pro Thr Ala Pro Pro
            115                 120                 125

Ser Gly Lys Arg Gly Asn Tyr Pro Val Gln Gln Ala Gly Gly Asn Tyr
130                 135                 140

Val His Val Pro Leu Ser Pro Arg Thr Leu Asn Ala Trp Val Lys Leu
145                 150                 155                 160

Val Glu Glu Lys Lys Phe Gly Ala Glu Val Val Pro Gly Phe Gln Ala
                165                 170                 175

Leu Ser Glu Gly Cys Thr Pro Tyr Asp Ile Asn Gln Met Leu Asn Cys
            180                 185                 190

Val Gly Asp His Gln Ala Ala Met Gln Ile Ile Arg Glu Ile Ile Asn
            195                 200                 205

Glu Glu Ala Ala Asp Trp Asp Ser Gln His Pro Ile Pro Gly Pro Leu
210                 215                 220

Pro Ala Gly Gln Leu Arg Asp Pro Arg Gly Ser Asp Ile Ala Gly Thr
225                 230                 235                 240

Thr Ser Thr Val Asp Glu Gln Ile Gln Trp Met Tyr Arg Pro Gln Asn
                245                 250                 255

Pro Val Pro Val Gly Asn Ile Tyr Arg Arg Trp Ile Gln Ile Gly Leu
            260                 265                 270

Gln Lys Cys Val Arg Lys Tyr Asn Pro Thr Asn Ile Leu Asp Ile Lys
        275                 280                 285

Gln Gly Pro Lys Glu Pro Phe Gln Ser Tyr Val Asp Arg Phe Tyr Lys
    290                 295                 300

Ser Leu Arg Ala Glu Gln Thr Asp Pro Ala Val Lys Asn Trp Met Thr
305                 310                 315                 320

Gln Thr Leu Leu Ile Gln Asn Ala Asn Pro Asp Cys Lys Leu Val Leu
                325                 330                 335

Lys Gly Leu Gly Met Asn Pro Thr Leu Glu Glu Met Leu Thr Ala Cys
            340                 345                 350

Gln Gly Val Gly Gly Pro Gly Gln Lys Ala Arg Leu Met Ala Glu Ala
            355                 360                 365

Leu Lys Glu Ala Met Gly Pro Ser Pro Ile Pro Phe Ala Ala Ala Gln
370                 375                 380

Gln Arg Lys Ala Ile Arg Tyr Trp Asn Cys Gly Lys Glu Gly His Ser
385                 390                 395                 400

Ala Arg Gln Cys Arg Ala Pro Arg Arg Gln Gly Cys Trp Lys Cys Gly
                405                 410                 415

Lys Pro Gly His Ile Met Ala Asn Cys Pro Glu Arg Gln Ala Gly Phe
            420                 425                 430

Leu Gly Leu Gly Pro Arg Gly Lys Lys Pro Arg Asn Phe Pro Val Thr
            435                 440                 445

Gln Ala Pro Gln Gly Leu Ile Pro Thr Ala Pro Pro Ala Asp Pro Ala
    450                 455                 460

Ala Glu Leu Leu Glu Arg Tyr Met Gln Gln Gly Arg Lys Gln Arg Glu
465                 470                 475                 480

Gln Arg Glu Arg Pro Tyr Lys Glu Val Thr Glu Asp Leu Leu His Leu
                485                 490                 495

Glu Gln Arg Glu Thr Pro His Arg Glu Glu Thr Glu Asp Leu Leu His
            500                 505                 510

Leu Asn Ser Leu Phe Gly Lys Asp Gln
            515                 520
```

<210> SEQ ID NO: 5
<211> LENGTH: 510
<212> TYPE: PRT
<213> ORGANISM: Simian Immunodeficiency Virus

<400> SEQUENCE: 5

```

```
Gln Gln Gly Arg Arg Thr Val Lys Cys Trp Asn Cys Gly Lys Glu Gly
385                 390                 395                 400

His Thr Ala Lys Gln Cys Lys Ala Pro Arg Arg Gln Gly Cys Trp Lys
            405                 410                 415

Cys Gly Lys Pro Gly His Gln Met Ala Lys Cys Pro Glu Arg Gln Val
            420                 425                 430

Gly Phe Leu Gly Phe Gly Pro Trp Gly Lys Lys Pro Arg Asn Phe Pro
            435                 440                 445

Met Ala Gln Ile Pro Gln Gly Leu Thr Pro Thr Ala Pro Pro Glu Met
    450                 455                 460

Pro Thr Ala Pro Pro Val Asp Pro Ala Ala Asp Leu Leu Arg Ser Tyr
465                 470                 475                 480

Met Gln Leu Gly Lys Lys Gln Arg Glu Ser Arg Lys Thr Pro Tyr Lys
                485                 490                 495

Glu Val Thr Glu Asp Leu Val His Leu Asn Ser Leu Phe Gly
            500                 505                 510

<210> SEQ ID NO: 6
<211> LENGTH: 429
<212> TYPE: PRT
<213> ORGANISM: Human T-Cell Lymphotrophic Virus Type 1

<400> SEQUENCE: 6

Met Gly Gln Ile Phe Ser Arg Ser Ala Ser Pro Ile Pro Arg Pro Pro
1               5                   10                  15

Arg Gly Leu Ala Ala His His Trp Leu Asn Phe Leu Gln Ala Ala Tyr
            20                  25                  30

Arg Leu Glu Pro Gly Pro Ser Ser Tyr Asp Phe His Gln Leu Lys Lys
        35                  40                  45

Phe Leu Lys Ile Ala Leu Glu Thr Pro Val Trp Ile Cys Pro Ile Asn
    50                  55                  60

Tyr Ser Leu Leu Ala Ser Leu Leu Pro Lys Gly Tyr Pro Gly Arg Val
65                  70                  75                  80

Asn Glu Ile Leu His Ile Leu Ile Gln Thr Gln Ala Gln Ile Pro Ser
                85                  90                  95

Arg Pro Ala Pro Pro Pro Ser Pro Thr His Asp Pro Pro Asp
            100                 105                 110                 Asp

Ser Asp Pro Gln Ile Pro Pro Pro Tyr Val Glu Pro Thr Ala Pro Gln
        115                 120                 125

Val Leu Pro Val Met His Pro His Gly Ala Pro Pro Asn His Arg Pro
130                 135                 140

Trp Gln Met Lys Asp Leu Gln Ala Ile Lys Gln Glu Val Ser Gln Ala
145                 150                 155                 160

Ala Pro Gly Ser Pro Gln Phe Met Gln Thr Ile Arg Leu Ala Val Gln
                165                 170                 175

Gln Phe Asp Pro Thr Ala Lys Asp Leu Gln Asp Leu Leu Gln Tyr Leu
            180                 185                 190

Cys Ser Ser Leu Val Ala Ser Leu His His Gln Gln Leu Asp Ser Leu
        195                 200                 205

Ile Ser Glu Ala Glu Thr Arg Gly Ile Thr Ser Tyr Asn Pro Leu Ala
    210                 215                 220

Gly Pro Leu Arg Val Gln Ala Asn Asn Pro Gln Gln Gln Gly Leu Arg
225                 230                 235                 240

Arg Glu Tyr Gln Gln Leu Trp Leu Ala Ala Phe Ala Ala Leu Pro Gly
```

-continued

```
                    245                 250                 255
Ser Ala Lys Asp Pro Ser Trp Ala Ser Ile Leu Gln Gly Leu Glu Glu
                260                 265                 270

Pro Tyr His Ala Phe Val Glu Arg Leu Asn Ile Ala Leu Asp Asn Gly
            275                 280                 285

Leu Pro Glu Gly Thr Pro Lys Asp Pro Ile Leu Arg Ser Leu Ala Tyr
        290                 295                 300

Ser Asn Ala Asn Lys Glu Cys Gln Lys Leu Leu Gln Ala Arg Gly His
305                 310                 315                 320

Thr Asn Ser Pro Leu Gly Asp Met Leu Arg Ala Cys Gln Thr Trp Thr
                325                 330                 335

Pro Lys Asp Lys Thr Lys Val Leu Val Val Gln Pro Lys Lys Pro Pro
            340                 345                 350

Pro Asn Gln Pro Cys Phe Arg Cys Gly Lys Ala Gly His Trp Ser Arg
        355                 360                 365

Asp Cys Thr Gln Pro Arg Pro Pro Gly Pro Cys Pro Leu Cys Gln
    370                 375                 380

Asp Pro Thr His Trp Lys Arg Asp Cys Pro Arg Leu Lys Pro Thr Ile
385                 390                 395                 400

Pro Glu Pro Glu Pro Glu Glu Asp Ala Leu Leu Leu Asp Leu Pro Ala
                405                 410                 415

Asp Ile Pro His Pro Lys Asn Ser Ile Gly Gly Glu Val
            420                 425
```

<210> SEQ ID NO: 7
<211> LENGTH: 657
<212> TYPE: PRT
<213> ORGANISM: Mason-Pfizer Monkey Virus

<400> SEQUENCE: 7

```
Met Gly Gln Glu Leu Ser Gln His Glu Arg Tyr Val Glu Gln Leu Lys
  1               5                  10                  15

Gln Ala Leu Lys Thr Arg Gly Val Lys Val Lys Tyr Ala Asp Leu Leu
                 20                  25                  30

Lys Phe Phe Asp Phe Val Lys Asp Thr Cys Pro Trp Phe Pro Gln Glu
             35                  40                  45

Gly Thr Ile Asp Ile Lys Arg Trp Arg Arg Val Gly Asp Cys Phe Gln
         50                  55                  60

Asp Tyr Tyr Asn Thr Phe Gly Pro Glu Lys Val Pro Val Thr Ala Phe
 65                  70                  75                  80

Ser Tyr Trp Asn Leu Ile Lys Glu Leu Ile Asp Lys Lys Glu Val Asn
                 85                  90                  95

Pro Gln Val Met Ala Ala Val Ala Gln Thr Glu Glu Ile Leu Lys Ser
            100                 105                 110

Asn Ser Gln Thr Asp Leu Thr Lys Thr Ser Gln Asn Pro Asp Leu Asp
        115                 120                 125

Leu Ile Ser Leu Asp Ser Asp Glu Gly Ala Lys Ser Ser Ser Leu
    130                 135                 140

Gln Asp Lys Gly Leu Ser Ser Thr Lys Pro Lys Arg Phe Pro Val
145                 150                 155                 160

Leu Leu Thr Ala Gln Thr Ser Lys Asp Pro Glu Asp Pro Asn Pro Ser
                165                 170                 175

Glu Val Asp Trp Asp Gly Leu Glu Asp Glu Ala Ala Lys Tyr His Asn
            180                 185                 190
```

```
Pro Asp Trp Pro Pro Phe Leu Thr Arg Pro Pro Tyr Asn Lys Ala
            195                 200                 205

Thr Pro Ser Ala Pro Thr Val Met Ala Val Val Asn Pro Lys Glu Glu
    210                 215                 220

Leu Lys Glu Lys Ile Ala Gln Leu Glu Glu Gln Ile Lys Leu Glu Glu
225                 230                 235                 240

Leu His Gln Ala Leu Ile Ser Lys Leu Gln Lys Leu Lys Thr Gly Asn
                245                 250                 255

Glu Thr Val Thr His Pro Asp Thr Ala Gly Gly Leu Ser Arg Thr Pro
            260                 265                 270

His Trp Pro Gly Gln His Ile Pro Lys Gly Lys Cys Cys Ala Ser Arg
        275                 280                 285

Glu Lys Glu Glu Gln Ile Pro Lys Asp Ile Phe Pro Val Thr Glu Thr
        290                 295                 300

Val Asp Gly Gln Gly Gln Ala Trp Arg His His Asn Gly Phe Asp Phe
305                 310                 315                 320

Ala Val Ile Lys Glu Leu Lys Thr Ala Ala Ser Gln Tyr Gly Ala Thr
                325                 330                 335

Ala Pro Tyr Thr Leu Ala Ile Val Glu Ser Val Ala Asp Asn Trp Leu
            340                 345                 350

Thr Pro Thr Asp Trp Asn Thr Leu Val Arg Ala Val Leu Ser Gly Gly
            355                 360                 365

Asp His Leu Leu Trp Lys Ser Glu Phe Phe Glu Asn Cys Arg Asp Thr
        370                 375                 380

Ala Lys Arg Asn Gln Gln Ala Gly Asn Gly Trp Asp Phe Asp Met Leu
385                 390                 395                 400

Thr Gly Ser Gly Asn Tyr Ser Ser Thr Asp Ala Gln Met Gln Tyr Asp
                405                 410                 415

Pro Gly Leu Phe Ala Gln Ile Gln Ala Ala Thr Lys Ala Trp Arg
            420                 425                 430

Lys Leu Pro Val Lys Gly Asp Pro Gly Ala Ser Leu Thr Gly Val Lys
        435                 440                 445

Gln Gly Pro Asp Glu Pro Phe Ala Asp Phe Val His Arg Leu Ile Thr
    450                 455                 460

Thr Ala Gly Arg Ile Phe Gly Ser Ala Glu Ala Gly Val Asp Tyr Val
465                 470                 475                 480

Lys Gln Leu Ala Tyr Glu Asn Ala Asn Pro Ala Cys Gln Ala Ala Ile
                485                 490                 495

Arg Pro Tyr Arg Lys Lys Thr Asp Leu Thr Gly Tyr Ile Arg Leu Cys
            500                 505                 510

Ser Asp Ile Gly Pro Ser Tyr Gln Gln Gly Leu Ala Met Ala Ala Ala
        515                 520                 525

Phe Ser Gly Gln Thr Val Lys Asp Phe Leu Asn Asn Lys Asn Lys Glu
    530                 535                 540

Lys Gly Gly Cys Cys Phe Lys Cys Gly Lys Lys Gly His Phe Ala Lys
545                 550                 555                 560

Asn Cys His Glu His Ala His Asn Asn Ala Glu Pro Lys Val Pro Gly
                565                 570                 575

Leu Cys Pro Arg Cys Lys Arg Gly Lys His Trp Ala Asn Glu Cys Lys
            580                 585                 590

Ser Lys Thr Asp Asn Gln Gly Asn Pro Ile Pro Pro His Gln Gly Asn
        595                 600                 605

Gly Trp Arg Gly Gln Pro Gln Ala Pro Lys Gln Ala Tyr Gly Ala Val
```

```
                610             615             620
Ser Phe Val Pro Ala Asn Lys Asn Pro Phe Gln Ser Leu Pro Glu
625                 630                 635                 640

Pro Pro Gln Glu Val Gln Asp Trp Thr Ser Val Pro Pro Thr Gln
                645                 650                 655

Tyr

<210> SEQ ID NO: 8
<211> LENGTH: 591
<212> TYPE: PRT
<213> ORGANISM: Mouse Mammary Tumor Virus

<400> SEQUENCE: 8

Met Gly Val Ser Gly Ser Lys Gly Gln Lys Leu Phe Val Ser Val Leu
1               5                   10                  15

Gln Arg Leu Leu Ser Glu Arg Gly Leu His Val Lys Glu Ser Ser Ala
            20                  25                  30

Ile Glu Phe Tyr Gln Phe Leu Ile Lys Val Ser Pro Trp Phe Pro Glu
        35                  40                  45

Glu Gly Gly Leu Asn Leu Gln Asp Trp Lys Arg Val Gly Arg Glu Met
    50                  55                  60

Lys Arg Tyr Ala Ala Glu His Gly Thr Asp Ser Ile Pro Lys Gln Ala
65                  70                  75                  80

Tyr Pro Ile Trp Leu Gln Leu Arg Glu Ile Leu Thr Glu Gln Ser Asp
                85                  90                  95

Leu Val Leu Leu Ser Ala Glu Ala Lys Ser Val Thr Glu Glu Glu Leu
            100                 105                 110

Glu Glu Gly Leu Thr Gly Leu Leu Ser Thr Ser Ser Gln Glu Lys Thr
        115                 120                 125

Tyr Gly Thr Arg Gly Thr Ala Tyr Ala Glu Ile Asp Thr Glu Val Asp
    130                 135                 140

Lys Leu Ser Glu His Ile Tyr Asp Glu Pro Tyr Glu Glu Lys Glu Lys
145                 150                 155                 160

Ala Asp Lys Asn Glu Glu Lys Asp His Val Arg Lys Ile Lys Lys Val
                165                 170                 175

Val Gln Arg Lys Glu Asn Ser Glu Gly Lys Arg Lys Glu Lys Asp Ser
            180                 185                 190

Lys Ala Phe Leu Ala Thr Asp Trp Asn Asp Asp Leu Ser Pro Glu
        195                 200                 205

Asp Trp Asp Asp Leu Glu Glu Gln Ala Ala His Tyr His Asp Asp Asp
    210                 215                 220

Glu Leu Ile Leu Pro Val Lys Arg Lys Val Val Lys Lys Pro Gln
225                 230                 235                 240

Ala Leu Arg Arg Lys Pro Leu Pro Pro Val Gly Phe Ala Gly Ala Met
                245                 250                 255

Ala Glu Ala Arg Glu Lys Gly Asp Leu Thr Phe Thr Phe Pro Val Val
            260                 265                 270

Phe Met Gly Glu Ser Asp Glu Asp Thr Pro Val Trp Glu Pro Leu
        275                 280                 285

Pro Leu Lys Thr Leu Lys Glu Leu Gln Ser Ala Val Arg Thr Met Gly
    290                 295                 300

Pro Ser Ala Pro Tyr Thr Leu Gln Val Val Asp Met Val Ala Ser Gln
305                 310                 315                 320

Trp Leu Thr Pro Ser Asp Trp His Gln Thr Ala Arg Ala Thr Leu Ser
```

```
                        325                 330                 335
Pro Gly Asp Tyr Val Leu Trp Arg Thr Glu Tyr Glu Lys Ser Lys
                340                 345                 350

Glu Met Val Gln Lys Ala Ala Gly Lys Arg Lys Gly Lys Val Ser Leu
            355                 360                 365

Asp Met Leu Leu Gly Thr Gly Gln Phe Leu Ser Pro Ser Ser Gln Ile
        370                 375                 380

Lys Leu Ser Lys Asp Val Leu Lys Asp Val Thr Thr Asn Ala Val Leu
385                 390                 395                 400

Ala Trp Arg Ala Ile Pro Pro Gly Val Lys Lys Thr Val Leu Ala
                405                 410                 415

Gly Leu Lys Gln Gly Asn Glu Glu Ser Tyr Glu Thr Phe Ile Ser Arg
                420                 425                 430

Leu Glu Glu Ala Val Tyr Arg Met Met Pro Arg Gly Glu Gly Ser Asp
            435                 440                 445

Ile Leu Ile Lys Gln Leu Ala Trp Glu Asn Ala Asn Ser Leu Cys Gln
        450                 455                 460

Asp Leu Ile Arg Pro Ile Arg Lys Thr Gly Thr Ile Gln Asp Tyr Ile
465                 470                 475                 480

Arg Ala Cys Leu Asp Ala Ser Pro Ala Val Val Gln Gly Met Ala Tyr
                485                 490                 495

Ala Ala Ala Met Arg Gly Gln Lys Tyr Ser Thr Phe Val Lys Gln Thr
            500                 505                 510

Tyr Gly Gly Gly Lys Gly Gly Gln Gly Ala Glu Gly Pro Val Cys Phe
        515                 520                 525

Ser Cys Gly Lys Thr Gly His Ile Arg Lys Asp Cys Lys Asp Glu Lys
        530                 535                 540

Gly Ser Lys Arg Ala Pro Pro Gly Leu Cys Pro Arg Cys Lys Lys Gly
545                 550                 555                 560

Tyr His Trp Lys Ser Glu Cys Lys Ser Lys Phe Asp Lys Asp Gly Asn
                565                 570                 575

Pro Leu Pro Pro Leu Glu Thr Asn Ala Glu Asn Ser Lys Asn Leu
                580                 585                 590

<210> SEQ ID NO: 9
<211> LENGTH: 538
<212> TYPE: PRT
<213> ORGANISM: Moloney Murine Leukemia Virus

<400> SEQUENCE: 9

Met Gly Gln Thr Val Thr Thr Pro Leu Ser Leu Thr Leu Asp His Trp
 1               5                  10                  15

Lys Asp Val Glu Arg Leu Ala His Asn Gln Ser Val Asp Val Lys Lys
                20                  25                  30

Arg Arg Trp Val Thr Phe Cys Ser Ala Glu Trp Pro Thr Phe Asn Val
            35                  40                  45

Gly Trp Pro Arg Asp Gly Thr Phe Asn Arg Asp Leu Ile Thr Gln Val
        50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Leu Pro Ser
                100                 105                 110
```

```
Ala Pro Ser Leu Pro Leu Glu Pro Pro Leu Ser Thr Pro Pro Gln Ser
        115                 120                 125

Ser Leu Tyr Pro Ala Leu Thr Pro Ser Leu Gly Ala Lys Pro Lys Pro
        130                 135                 140

Gln Val Leu Ser Asp Ser Gly Gly Pro Leu Ile Asp Leu Leu Thr Glu
145                 150                 155                 160

Asp Pro Pro Tyr Arg Asp Pro Arg Pro Pro Ser Asp Arg Asp
                165                 170                 175

Gly Asp Ser Gly Glu Ala Thr Pro Ala Gly Glu Ala Pro Asp Pro Ser
            180                 185                 190

Pro Met Ala Ser Arg Leu Arg Gly Arg Glu Pro Pro Val Ala Asp
        195                 200                 205

Ser Thr Thr Ser Gln Ala Phe Pro Leu Arg Thr Gly Gly Asn Gly Gln
210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
290                 295                 300

Pro Asn Glu Val Asp Ala Ala Phe Pro Leu Glu Arg Pro Asp Trp Glu
305                 310                 315                 320

Tyr Thr Thr Gln Ala Gly Arg Asn His Leu Val His Tyr Arg Gln Leu
                325                 330                 335

Leu Ile Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Arg
                405                 410                 415

Asn Lys Thr Leu Gly Asp Leu Val Arg Glu Ala Glu Arg Ile Phe Asn
            420                 425                 430

Lys Arg Glu Thr Pro Glu Glu Arg Glu Arg Ile Arg Arg Glu Arg
        435                 440                 445

Glu Glu Lys Glu Glu Arg Arg Thr Glu Asp Glu Gln Lys Glu Lys
450                 455                 460

Glu Arg Asp Arg Arg His Arg Glu Met Ser Arg Leu Leu Ala Thr
465                 470                 475                 480

Val Val Ser Gly Gln Arg Gln Asp Arg Gln Glu Gly Glu Arg Arg
                485                 490                 495

Ser Gln Leu Asp Cys Asp Gln Cys Thr Tyr Cys Glu Glu Gln Gly His
            500                 505                 510

Trp Ala Lys Asp Cys Pro Arg Arg Pro Arg Gly Pro Arg Gly Pro Arg
        515                 520                 525

Pro Gln Thr Ser Leu Leu Thr Leu Asp Asp
```

```
<210> SEQ ID NO: 10
<211> LENGTH: 701
<212> TYPE: PRT
<213> ORGANISM: Rous Sarcoma Virus

<400> SEQUENCE: 10

Met Glu Ala Val Ile Lys Val Ile Ser Ser Ala Cys Lys Thr Tyr Cys
 1               5                  10                  15

Gly Lys Thr Ser Pro Ser Lys Lys Glu Ile Gly Ala Met Leu Ser Leu
            20                  25                  30

Leu Gln Lys Glu Gly Leu Leu Met Ser Pro Ser Asp Leu Tyr Ser Pro
        35                  40                  45

Gly Ser Trp Asp Pro Ile Thr Ala Ala Leu Thr Gln Arg Ala Met Val
    50                  55                  60

Leu Gly Lys Ser Gly Glu Leu Lys Thr Trp Gly Leu Val Leu Gly Ala
65                  70                  75                  80

Leu Lys Ala Ala Arg Glu Glu Gln Val Thr Ser Glu Gln Ala Lys Phe
                85                  90                  95

Trp Leu Gly Leu Gly Gly Gly Arg Val Ser Pro Pro Gly Pro Glu Cys
            100                 105                 110

Ile Glu Lys Pro Ala Thr Glu Arg Arg Ile Asp Lys Gly Glu Glu Val
        115                 120                 125

Gly Glu Thr Thr Val Gln Arg Asp Ala Lys Met Ala Pro Glu Glu Thr
    130                 135                 140

Ala Thr Pro Lys Thr Val Gly Thr Ser Cys Tyr His Cys Gly Thr Ala
145                 150                 155                 160

Ile Gly Cys Asn Cys Ala Thr Ala Ser Ala Pro Pro Pro Pro Tyr Val
                165                 170                 175

Gly Ser Gly Leu Tyr Pro Ser Leu Ala Gly Val Gly Glu Gln Gln Gly
            180                 185                 190

Gln Gly Gly Asp Thr Pro Arg Gly Ala Glu Gln Pro Arg Ala Glu Pro
        195                 200                 205

Gly His Ala Gly Leu Ala Pro Gly Pro Ala Leu Thr Asp Trp Ala Arg
    210                 215                 220

Ile Arg Glu Glu Leu Ala Ser Thr Gly Pro Pro Val Val Ala Met Pro
225                 230                 235                 240

Val Val Ile Lys Thr Glu Gly Pro Ala Trp Thr Pro Leu Glu Pro Lys
                245                 250                 255

Leu Ile Thr Arg Leu Ala Asp Thr Val Arg Thr Lys Gly Leu Arg Ser
            260                 265                 270

Pro Ile Thr Met Ala Glu Met Glu Ala Leu Met Ser Ser Pro Leu Leu
        275                 280                 285

Pro His Asp Val Thr Asn Leu Met Arg Val Ile Leu Gly Pro Ala Pro
    290                 295                 300

Tyr Ala Leu Trp Met Asp Ala Trp Gly Val Gln Leu Gln Thr Val Ile
305                 310                 315                 320

Ala Ala Ala Thr Arg Asp Pro Arg His Pro Ala Asn Gly Gln Gly Arg
                325                 330                 335

Gly Glu Arg Thr Asn Leu Asp Arg Leu Lys Gly Leu Ala Asp Gly Met
            340                 345                 350

Val Gly Asn Ser Glu Gly Gln Ala Ala Leu Leu Arg Pro Gly Glu Leu
        355                 360                 365
```

-continued

```
Val Ala Ile Thr Ala Ser Ala Leu Gln Ala Phe Arg Glu Val Ala Arg
    370             375             380
Leu Ala Glu Pro Thr Asp Pro Trp Ala Asp Ile Met Gln Gly Pro Ser
385             390             395             400
Glu Ser Phe Val Asp Phe Ala Asn Arg Leu Ile Lys Ala Val Glu Gly
                405             410             415
Ser Asp Leu Pro Pro Ser Ala Arg Ala Pro Val Ile Ile Asp Cys Phe
            420             425             430
Arg Gln Lys Ser Gln Pro Asp Ile Gln Gln Leu Ile Arg Ala Ala Pro
        435             440             445
Ser Thr Leu Thr Thr Pro Gly Glu Ile Ile Lys Tyr Val Leu Asp Arg
    450             455             460
Gln Lys Thr Ala Pro Leu Thr Asp Gln Gly Ile Ala Ala Ala Met Ser
465             470             475             480
Ser Ala Ile Gln Pro Leu Val Met Ala Val Val Asn Arg Glu Arg Asp
                485             490             495
Gly Gln Thr Gly Ser Gly Gly Arg Ala Arg Glu Leu Cys Tyr Thr Cys
            500             505             510
Gly Ser Pro Gly His Tyr Gln Ala Gln Cys Pro Lys Lys Arg Lys Ser
        515             520             525
Gly Asn Ser Arg Glu Arg Cys Gln Leu Cys Asn Gly Met Gly His Asn
    530             535             540
Ala Lys Gln Cys Arg Lys Arg Asp Gly Asn Gln Gly Gln Arg Pro Gly
545             550             555             560
Arg Gly Leu Ser Ser Gly Pro Trp Pro Gly Pro Glu Pro Pro Ala Val
                565             570             575
Ser Leu Ala Met Thr Met Glu His Lys Asp Arg Pro Leu Val Arg Val
            580             585             590
Ile Leu Thr Asn Thr Gly Ser His Pro Val Lys Gln Arg Ser Val Tyr
        595             600             605
Ile Thr Ala Leu Leu Asp Ser Gly Ala Asp Ile Thr Ile Ile Ser Glu
    610             615             620
Glu Asp Trp Pro Thr Asp Trp Pro Val Met Glu Ala Ala Asn Pro Gln
625             630             635             640
Ile His Gly Ile Gly Gly Ile Pro Met Arg Lys Ser Arg Asp Met
                645             650             655
Ile Glu Leu Gly Val Ile Asn Arg Asp Gly Ser Leu Glu Arg Pro Leu
            660             665             670
Leu Leu Phe Pro Ala Val Ala Met Val Arg Gly Ser Ile Leu Gly Arg
        675             680             685
Asp Cys Leu Gln Gly Leu Gly Leu Arg Leu Thr Asn Leu
    690             695             700
```

PEPTIDES THAT BLOCK VIRAL INFECTIVITY AND METHODS OF USE THEREOF

FIELD OF THE INVENTION

The present invention is related to the discovery of peptides that inhibit viral infection, including human immunodeficiency virus (HIV) infection. More specifically, medicaments comprising various small peptides are disclosed for use in the treatment and prevention of viral infection, such as HIV infection.

BACKGROUND OF THE INVENTION

All viruses are composed of a protein shell surrounding a nucleic acid containing core. The protein shell directly surrounding the viral nucleic acid is called a capsid, whereas, the complete protein-nucleic acid complex having both the capsid and the nucleic acid is called a nucleocapsid. Arenaviruses, rotaviruses, orbiviruses, retroviruses (including lentiviruses), papillomaviruses, adenoviruses, herpesviruses, paramyxovirus, myxovirus, and hepadnaviruses all exhibit these general structural features. (*Virolog*, Fields ed., third edition, Lippencott-Raven publishers, pp 1513, 1645,1778, 2047, 2113, 2221, and 2717 (1996)).

The capsid is composed of many subunits (capsomeres) and capsomeres are formed from several homo or hetero-polymers of protein. The noncovalent bonds between capsomeres in a viral assembly are of the same sort that stabilize a folded protein domain. The interface between two subunits can look very much like a single domain, with amino acid side chains tightly packed against one another. A common feature to most of the virus structures analyzed is the way in which a polypeptide chain from one capsomere can extend under or over domains of neighboring capsomeres. These extended polypeptide arms intertwine with other polypeptide arms and help to stabilize the capsid by initiating hydrophobic interactions, hydrogen bonding, and salt bridges. Contacts between individual capsomeres, and for some viruses also contacts with core proteins, determine the overall capsid structure and if a number of identical capsomeres are involved, repeated contacts occur and the resulting structure is symmetrical. (*Virology*, Fields ed., third edition, Lippencott-Raven publishers, p 62 (1996)).

Some simple viruses form spontaneously from their dissociated components while others require enzyme-catalyzed modifications of the capsomeres to trigger assembly. Viral self assembly is driven by the stability of the interactions between protein subunits under conditions that favor association. More complex viruses are often constructed from subassemblies that have undergone self assembly processes. (*Virolog*, Fields ed., third edition, Lippencott-Raven publishers, pp 62, 70, 1646 and 1888 (1996)). Although the capsids of many viruses differ in protein composition, a general viral structural design has evolved characterized by polymerized capsomeres that, in turn, are composed of several homo- or hetero-polymers of protein.

HIV is the name given to a lentivirus that infects humans and that causes acquired immuno-deficiency syndrome (AIDS). The lentivirus isolates from humans are grouped into one of two types (HIV-1 and HIV-2) on the basis of serologic properties and sequence analysis of molecularly cloned viral genomes. Genetically distinct lentiviruses have been obtained from several non-human primate species including African green monkeys, sooty magabeys, mandrills, chimpanzees, and sykes. Collectively, the lentivirus isolates from non-human primates are called SIV.

Sequence analysis reveals that the genomes of some SIV strains and HIV-1 and HIV-2 strains exhibit a high degree of homology. Further, electron microscopy reveals that the ultrastructure of HIV and SIV are similar in that both have virions about 110 nm in diameter with a cone-shaped nucleocapsid surrounded by a lipid bilayer membrane that contains envelope glycoprotein spikes. (*Virology*, Fields ed., third edition, Lippencott-Raven publishers, pp 1882–1883 (1996)).

HIV is a complex retrovirus containing at least seven genes. The viral structural genes, designated gag, pol, and env, respectively code for the viral core proteins, reverse transcriptase, and the viral glycoproteins of the viral envelope. The remaining HIV genes are accessory genes involved in viral replication. The gag and env genes encode polyproteins, i.e., the proteins synthesized from each of these genes are post-translationally cleaved into several smaller proteins.

Although the overall shape of HIV and SIV virions is spherical, the nucleocapsid is asymmetrical having a long dimension of about 100 nm, a wide free end about 40–60 nm, and a narrow end about 20 nm in width. The nucleocapsid within each mature virion is composed of two molecules of the viral single-stranded RNA genome encapsulated by proteins proteolytically processed from the Gag precursor polypeptide. Cleavage of the gag gene polyprotein Pr55$^{gag}$ by a viral coded protease (PR) produces mature capsid proteins. These gag gene products are the matrix protein (p17), that is thought to be located between the nucleocapsid and the virion envelope; the major capsid protein (p24), that forms the capsid shell; and the nucleocapsid protein (p9), that binds to the viral RNA genome. This proteolytic processing in infected cells is linked to virion morphogenesis. (*Virology*, Fields ed., third edition, Lippencott-Raven publishers, pp 1886–1887 (1996)).

The major capsid protein p24 (also called CA) contains about 240 amino acids and exhibits a molecular weight of 24–27 kD. The protein p24 self-associates to form dimers and oligomeric complexes as large as dodecamers. Genetic studies with mutations in the HIV-1 gag polyprotein have identified several functional domains in the p24 protein including the C terminal half of the molecule and a major homology region (MHR) spanning 20 amino acids that is conserved in the p24 proteins of diverse retroviruses. These mutations appear to affect precursor nucleocapsid assembly. (*Virology*, Fields ed., third edition, Lippencott-Raven publishers, pp 1888–1889 (1996)).

Since the discovery of HIV-1 as the etiologic agent of AIDS, significant progress has been made in understanding the mechanisms by which the virus causes disease. While many diagnostic tests have been developed, progress in HIV vaccine therapy has been slow largely due to the heterogeneous nature of the virus and the lack of suitable animal models. (See, e.g., Martin, *Nature*, 345:572–573 (1990)).

A variety of pharmaceutical agents have been used in attempts to treat AIDS. Many, if not all, of these drugs, however, create serious side effects that greatly limit their usefulness as therapeutic agents. HIV reverse transcriptase is one drug target because of its crucial role in viral replication. Several nucleoside derivatives have been found to inhibit HIV reverse transcriptase including azidothymidine (AZT, zidovidine®). AZT causes serious side effects such that many patients cannot tolerate its administration. Other nucleoside analogs that inhibit HIV reverse transcriptase have been found to cause greater side effects than AZT. Another drug target is the HIV protease (PR) crucial to virus development. PR is an aspartic protease and can be inhibited by synthetic compounds. (Richards, *FEBS Lett.*, 253:214–216 (1989)). Protease inhibitors inhibit the growth of HIV more effectively than reverse transcriptase inhibitors but prolonged therapy has been associated with metabolic diseases such as lipodystrophy, hyperlipidemia, and insulin resistance.

Additionally, HIV quickly develops resistance to nucleoside/nucleotide analogue reverse transcriptase inhibitors and protease inhibitors. This resistance can also spread between patients. Studies have shown, for example, that one tenth of the individuals recently infected by HIV already have developed resistance to AZT, probably because they were infected by a person that at the time of transmission carried a virus that was resistant to AZT.

It would be useful in the treatment and prevention of viral infections, including HIV and SIV, to have specific and selective therapeutic agents that cause few, if any, side effects.

SUMMARY OF THE INVENTION

The present invention is related to small peptides (two to ten amino acids in length) that inhibit viral infectivity. An intact capsid structure is of vital importance for the infectivity of a virion. A way to disrupt assembly of capsid protein macromolecules, that for their infectivity are dependent on di-, tri-, tetra-, or polymerization, is to construct small molecules that affect such protein-protein interactions. It was discovered that small peptides with their carboxyl terminus hydroxyl group replaced with an amide group have such an inhibiting effect on capsid-protein interactions. Thus, aspects of the present invention relate to modified small peptides that effect viral capsid assembly.

In desirable embodiments, the short peptides bind to a protein that is involved in capsomere organization and capsid assembly of HIV-1, HIV-2, and SIV and thereby inhibit and/or prevent proper capsid assembly and, thus, viral infection. The small peptides Gly-Pro-Gly-$NH_2$ (GPG-$NH_2$), Gly-Lys-Gly-$NH_2$ (GKG-$NH_2$), Cys-Gln-Gly-$NH_2$ (CQG-$NH_2$), Arg-Gln-Gly-$NH_2$ (RQG-$NH_2$), Lys-Gln-Gly-$NH_2$ (KQG-$NH_2$), Ala-Leu-Gly-$NH_2$ (ALG-$NH_2$), Gly-Val-Gly-$NH_2$ (GVG-$NH_2$), Val-Gly-Gly-$NH_2$ (VGG-$NH_2$), Ala-Ser-Gly-$NH_2$ (ASG-$NH_2$), Ser-Leu-Gly-$NH_2$ (SLG-$NH_2$), and Ser-Pro-Thr-$NH_2$ (SPT-$NH_2$) are the preferred species. These small peptides and peptidomimetics resembling their structure (collectively referred to as "peptide agents") are used in a monomeric or multimeric form. The peptide agents of the present invention are suitable for therapeutic and prophylactic application in mammals, including man, suffering from viral infection.

In one embodiment, a composition for inhibiting viral replication in host cells infected with a virus has an effective amount of a peptide in amide form having the formula $X_1X_2X_3$-$NH_2$, wherein $X_1$, $X_2$, and $X_3$ are any amino acid and said peptide is not Gly-Pro-Gly-$NH_2$, and wherein said composition inhibits viral replication by interrupting viral capsid assembly. Desirably, $X_3$ of these peptides is glycine. Additionally, the compositions described above can include a peptide in amide form selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$.

In another related embodiment, the composition described above is a peptide in amide form that has the formula $X_{4\times 5}X_1X_2X_3$-$NH_2$, wherein $X_4$ and $X_5$ are any amino acid and any one or two amino acids can be absent. This embodiment can be a tripeptide having the formula $X_1X_2X_3$, wherein the sequence is found in the amino acid sequence of the capsid protein of the virus.

In some embodiments, the compositions described above are joined to a support and in other embodiments, the compositions described above are incorporated into a pharmaceutical having a pharmaceutically acceptable carrier. For example, the peptide in amide form can have the formula Gly-Lys-Gly-$NH_2$.and can be joined to a support. Further, the peptide in amide form can have a formula such as Arg-Gln-Gly-$NH_2$, Cys-Gln-Gly-$NH_2$, Lys-Gln-Gly-$NH_2$, Ala-Leu-Gly-$NH_2$, or Ser-Leu-Gly-$NH_2$. Thes peptides can also be joined to a support.

Methods of inhibiting HIV replication in a host cell are also embodiments. One approach, for example, involves administering to a cell an effective amount of a peptide in amide form having the formula $X_1X_2X_3$-$NH_2$, wherein $X_1$, $X_2$, and $X_3$ are any amino acid and said peptide is not Gly-Pro-Gly-$NH_2$. Accordingly, the peptide above can be selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$. The method described above can further include the step of administering an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. The peptide used in the method above can bejoined to a support or can be administered in a pharmaceutical comprising a pharmaceutically acceptable carrier.

In another embodiment, a composition for inhibiting HIV replication in host cells includes an effective amount of a peptide in amide form having the formula $X_1X_2X_3$-$NH_2$, wherein $X_1$, $X_2$, and $X_3$ are any amino acid and said peptide is not Gly-Pro-Gly-$NH_2$ and wherein said composition inhibits HIV replication by interrupting assembly of the capsid. Desirably, $X_3$ is glycine in the peptides of this embodiment. Preferably, the peptide of this embodiment is selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$. Additionally, the peptide in amide form, described above, can have the formula $X_4X_5X_1X_2X_3$-$NH_2$, wherein $X_4$ and $X_5$ are amino acids and wherein any one or two, amino acids is absent. These compositions can have a tripeptide $X_1X_2X_3$ that is found in the amino acid sequence of the capsid protein of HIV, for example. In some embodiments, these peptides are joined to a support and in other embodiments, these peptides are incorporated into a pharmaceutical comprising a pharmaceutically acceptable carrier.

In another method, an approach to inhibit viral replication in host cells is provided, which involves administering to said cells an effective amount of a peptide in amide form having the formula $X_1X_2X_3$-$NH_2$, wherein $X_1$, $X_2$, and $X_3$ are any amino acid and said peptide is not Gly-Pro-Gly-$NH_2$. In this method, the peptide can be selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$. This method can also include the step of administering an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. Further, the peptide used in this method can be joined to a support or can be administered in a pharmaceutical comprising a pharmaceutically acceptable carrier.

In another method, an approach for interrupting viral capsid assembly is provided. This approach involves contacting a cell with an effective amount of a peptide in amide form having the formula $X_1X_2X_3$-$NH_2$, wherein $X_1$, $X_2$, and $X_3$ are any amino acid and said peptide is not Gly-Pro-Gly-$NH_2$. Desirably, the peptide used in this method is selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$. In some embodiments, $X_3$ is glycine in the peptide used in this method. In other embodiments, the method employs a peptide in amide form having the formula $X_4X_5X_1X_2X_3$-$NH_2$, wherein $X_4$ and $X_5$ are an amino acid and, wherein any one or two amino acids is absent. Still further, the method can involve the use of a tripeptide $X_1X_2X_3$ that is found in the amino acid sequence of a protein of the virus. Oftentimes the peptide of the method is joined to a support or is incorporated in a pharmaceutical.

Methods of identification of peptide agents are also provided. By one method, for example, a peptide agent for incorporation into a anti-viral pharmaceutical is identified by contacting a plurality of cells infected with a virus with an effective amount of a peptide agent, wherein said peptide is not Gly-Pro-Gly-$NH_2$, analyzing the virus for incomplete capsid formation, and selecting the peptide agent that induces incomplete capsid formation. This method can involve an analysis of capsid formation that employs microscopy and the virus can be selected from the group consisting of HIV-1, HIV-2, and SIV. Further, the peptide agent identified can be selected from the group consisting of a tripeptide, an oligopeptide, and a peptidomimetic. For example, the peptide agent above can be selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$. In a preferred embodiment, the peptide agent used in the method above has an amino acid sequence that corresponds to an amino acid sequence of p24.

In another embodiment, a method for identifying a peptide agent that binds to a viral protein is provided, which involves providing a viral protein, contacting the viral protein with an effective amount of a peptide agent, wherein said peptide agent is not Gly-Pro-Gly-$NH_2$, and detecting the formation of a complex comprising the viral protein and the peptide agent. As above, this method can involve the use of a viral protein that is from a virus selected from the group consisting of HIV-1, HIV-2, and SIV. Further, in some aspects, the peptide agent is selected from the group consisting of a tripeptide, an oligopeptide, and a peptidomimetic. Desirably, the method above employs a peptide agent is selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$. Additionally, a method of making a pharmaceutical is provided in which the peptide agent identified by the methods above are incorporated in a pharmaceutical.

Another approach to make a pharmaceutical is also provided, which involves administering to a cell an effective amount of a peptide in amide form having the formula $X_1X_2X_3$-$NH_2$, wherein $X_1$, $X_2$, and $X_3$ are any amino acid and said peptide is not Gly-Pro-Gly-$NH_2$, detecting an inhibition of viral replication in the cell, and incorporating the peptide that causes inhibition of viral replication into the pharmaceutical. This method can involve the use of a peptide that is selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$. Further, the method above can involve the step of incorporating an antiviral compound selected from the group consisting of nucleoside analogue reverse transcriptase inhibitors, nucleotide analogue reverse transcriptase inhibitors, non-nucleoside reverse transcriptase inhibitors, and protease inhibitors into the pharmaceutical. Additionally, the method above can involve the step of incorporating a carrier into the pharmaceutical.

In another embodiment, a composition for inhibiting viral replication in host cells infected with a virus includes an effective amount of a peptide having the formula $X_1X_2X_3$-R, wherein $X_1$, $X_2$, and $X_3$ are any amino acid and said peptide is not Gly-Pro-Gly-$NH_2$, wherein R is a modulation group attached to the carboxy-terminus of said peptide and R comprises an amide group or other moiety having similar charge and steric bulk and wherein said composition inhibits viral replication by interrupting viral capsid assembly. This composition can be a peptide selected from the group consisting of peptides having the formula Gly-Lys-Gly-$NH_2$, Arg-Gln-Gly-$NH_2$, Cys-Gln-Gly-$NH_2$, Lys-Gln-Gly-$NH_2$, Ala-Leu-Gly-$NH_2$, Gly-Val-Gly-$NH_2$, Val-Gly-Gly-$NH_2$, Ala-Ser-Gly-$NH_2$, Ser-Leu-Gly-$NH_2$, and Ser-Pro-Thr-$NH_2$. Desirably, $X_3$ is glycine in these embodiments.

Additionally, the composition above can include a peptide that has the formula $X_4X_5X_6X_7X_8X_9X_{10}X_1X_2X_3$-R, wherein $X_4$, $X_5$, $X_6$, $X_7$, $X_8$, $X_9$, and $X_{10}$ are any amino acid and wherein any one, two, three, four, five, six, or seven amino acids is absent, wherein R is a modulation group attached to the carboxy-terminus of said peptide and R comprises an amide group or other moiety having similar charge and steric bulk. Preferably, the composition above includes a peptide $X_1X_2X_3$ that is found in the amino acid sequence of the capsid protein of the virus.

BRIEF DESCRIPTION OF THE DRAWINGS

FIG. 3 is a composite of electron micrographs of HIV particles that have been contacted with the protease inhibitor Ritonavir.

FIG. 5 illustrates an alignment of the protein sequence corresponding to the carboxyl terminus of the HIV-1 p24 protein (residues 146–231) and protein sequences of HIV-2, SIV, Rous Sarcoma virus (RSV), human T cell leukemia virus-type 1 (HTLV-1), mouse mammary tumor virus (MMTV), Mason-Pfizer monkey virus (MPMV), and Moloney murine leukemia virus (MMLV). The bar represents the major homology region (MHR).

DETAILED DESCRIPTION OF THE PREFERRED EMBODIMENT

Figure 1:
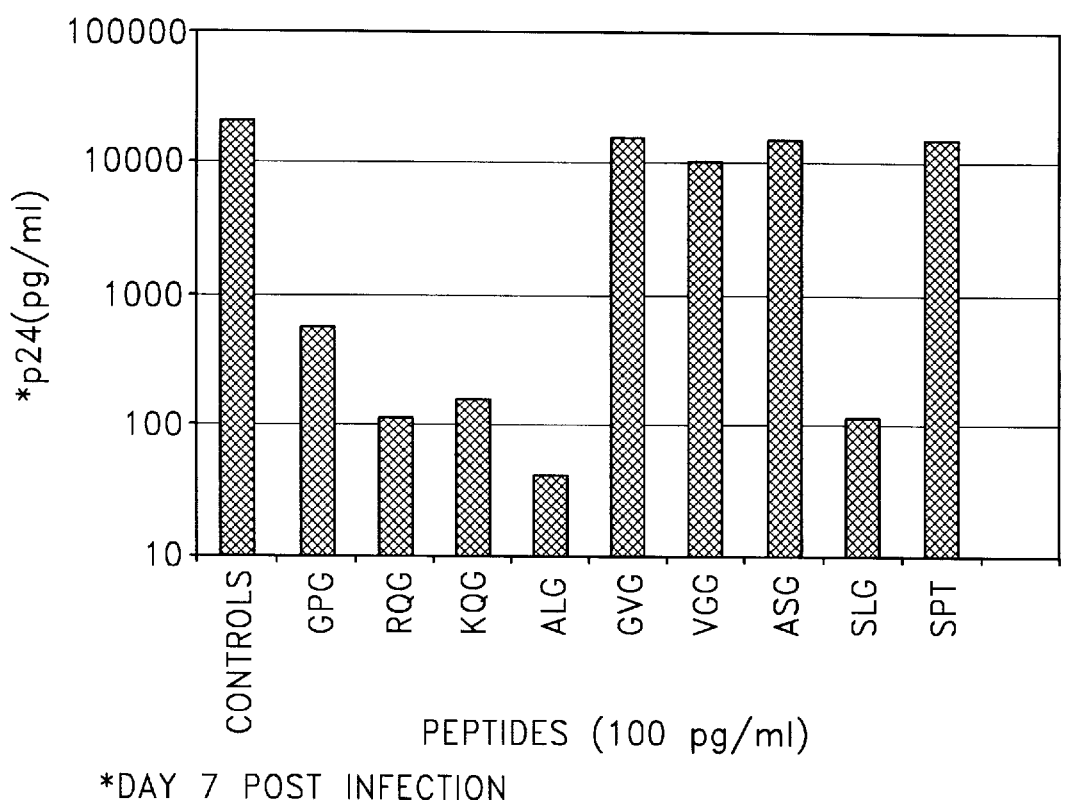
FIG. 1 is a graph representing the results from an HIV infectivity study conducted in HUT78 cells.

The inventor has discovered that modified small peptides having sequences that correspond to viral capsid proteins prevent and/or inhibit viral infection by interrupting proper nucleocapsid formation. Such peptides are useful in the treatment of viral disease, particularly in HIV/AIDS afflicted subjects, and as preventive agents for patients at-risk of viral infection, particularly HIV infection, and for use with medical devices where the risk of exposure to virus is significant.

In the disclosure below, the inventor demonstrates that small peptides in amide form that have a sequence that corresponds to viral proteins, such as GPG-NH$_2$, GKG-NH$_2$, CQG-NH$_2$, RQG-NH$_2$, KQG-NH$_2$, ALG-NH$_2$, GVG-NH$_2$, VGG-NH$_2$, ASG-NH$_2$, SLG-NH$_2$, and SPT-NH$_2$ inhibit the replication of viruses, such as HIV-1, HIV-2, and SIV, as measured by viral infectivity assays that monitor the amount of capsid protein or reverse transcriptase activity present in culture supematent. Further, the inventor presents evidence that these small peptides inhibit viral infectivity by a V3 loop independent mechanism at a stage subsequent to DNA, RNA, and protein synthesis.

Electron microscopic images of HIV particles treated with small peptides reveal that this novel class of antiviral agent interrupts proper capsid assembly in a manner distinct from protease inhibitors. Further, in vitro binding assays reveal that the small peptides bind to the major capsid protein (p24) of HIV-1. Because the sequences of several viral capsid proteins are known, such as members of arenavirus, rotavirus, orbivirus, retrovirus, papillomavirus, adenovirus, herpesvirus, paramyxovirus, myxovirus, and hepadnavirus families, several small peptides that correspond to these sequences can be selected and rapidly screened to identify which ones effectively inhibit and/or prevent viral infection by using the viral infectivity assays or electron microscopy techniques or both described herein, or modifications of these assays as would be apparent to those of skill in the art given the present disclosure.

Several approaches to make biotechnological tools and pharmaceutical compositions comprising small peptides and peptidomimetics (collectively referred to as "peptide agents") that correspond to sequences of viral capsid proteins are given below. Although preferable peptide agents are tripeptides having an amide group at their carboxy termini, such as GPG-NH$_2$, GKG-NH$_2$, CQG-NH$_2$, RQG-NH$_2$, KQG-NH$_2$, ALG-NH$_2$, GVG-NH$_2$, VGG-NH$_2$, ASG-NH$_2$, SLG-NH$_2$, and SPT-NH$_2$, the inventor also provides compositions and methods of inhibiting viral replication in host cells, including HIV replication in host cells, comprising a peptide in amide form having the formula $X_1$, $X_2$, $X_3$-NH$_2$ or the formula $X_4$, $X_5$, $X_1$, $X_2$, $X_3$-NH$_2$, wherein $X_1$, $X_2$, $X_3$, $X_4$, and $X_5$ are any amino acid and wherein any one or two amino acids can be absent. Preferred embodiments have a glycine residue as $X_3$. In some embodiments, the peptide agents are provided in monomeric form; in others, the peptide agents are provided in multimeric form or in multimerized form. Support-bound peptide agents are also used in several embodiments. Pharmaceutical compositions comprising peptide agents are administered as therapeutics or prophylactics or both for the treatment and/or prevention of viral disease, preferably, HIV infection. In some embodiments, the pharmaceutical compositions comprising peptide agents are administered in combination with other antiviral treatments including nucleoside analogue reverse transcriptase inhibitors, nucleotide analogue reverse transcriptase inhibitors, non-nucleoside reverse transcriptase inhibitors, and protease inhibitors. The inventor also provides evidence that small peptides are resistant to acid hydrolysis, that a significant amount of small peptide is effectively delivered to blood, plasma, and organ tissue when administered to test subjects, and that the administration of large doses of small peptides to test subjects is relatively nontoxic.

Additionally, the inventor discloses several methods of identifying a peptide agent that inhibits or prevents viral replication or interrupts viral capsid assembly or both. By one approach, an effective amount of a peptide agent is contacted with cells infected with a virus and the cells are analyzed for viral replication or the presence of viral products. Further, by using electron microscopy, the ability of a peptide agent to interupt capsid assembly can be readily determined. Still further, methods are disclosed that identify a peptide agent that binds to a capsid protein (e.g., p24) and thereby interupts capsid assembly and, thus, viral replication. Accordingly, a capsid protein (e.g., p24) is contacted with a peptide agent, for example a peptide in amide form having the formula $X_1$, $X_2$, $X_3$, wherein $X_1$, $X_2$, and $X_3$ are any amino acid, and a complex comprising the capsid protein (e.g., p24) bound with the peptide agent is identified. Reaction mixtures having a viral protein (e.g., p24) and a peptide agent and a biomolecular complex having a viral protein (e.g., p24) joined to a peptide agent are also taught in the present disclosure.

The amide form of small peptides listed in Table 1 below were tested. Many of these small peptides were selected and synthesized because they either fully or partially correspond to sequences in HIV and/or SIV viral proteins. The small peptides of Table 1 were synthesized according to the method disclosed in Example 1 below, but could of course be synthesized by any method known in the art.

TABLE 1

Amino Acid Sequence of Peptides Tested

| | |
|---|---|
| Leu-Lys-Ala (LKA) | Arg-Gln-Gly (RQG) |
| Iso-Leu-Lys (ILK) | Lys-Gln-Gly (KQG) |
| Gly-Pro-Gln (GPQ) | Ala-Leu-Gly (ALG) |
| Gly-His-Lys (GHK) | Gly-Val-Gly (GVG) |
| Gly-Lys-Gly (GKG) | Val-Gly-Gly (VGG) |
| Ala-Cys-Gln (ACQ) | Ala-Ser-Gly (ASG) |
| Cys-Gln-Gly (CQG) | Ser-Leu-Gly (SLG) |
| Ala-Arg-Val (ARV) | Ser-Pro-Thr (SPT) |
| Lys-Ala-Arg (KAR) | Gly-Ala-Thr (GAT) |
| His-Lys-Ala (HKA) | Lys-Ala-Leu (KAL) |
| Gly-Pro-Gly (GPG) | |

Abbreviations Used:

| | |
|---|---|
| Leu-Leucine | Lys-Lysine |
| Gln-Glutamine | Ala-Alanine |
| His-Histidine | Ileu-Isoleucine |
| Cys-Cysteine | Gly-Glycine |
| Pro-Proline | Arg-Arginine |
| Val-Valine | Thr-Threonine |
| Ser-Serine | |

EXAMPLE 1

In this example, the approaches used to obtain the small peptides listed above are disclosed. Several tripeptides were chemically synthesized with an automated peptide synthesizer (Syro, Multisyntech, Tubingen, Germany). The synthesis was run using 9-fluorenylmethoxycarbonyl (fmoc) protected amino acids (Milligen, Bedford, Mass.) according to standard protocols. All peptides were lyophilized and then disolved at the appropriate concentration in phosphate-buffered saline (PBS). The peptides were analyzed by reverse phase high performance liquid chromatography (RP-HPLC) using a PepS-15 C18 column (Pharmacia, Uppsala, Sweden).

In many embodiments, peptides having a modulation group attached to the carboxy-terminus of the peptide ("modified peptides") were used. In some cases, the modified peptides were created by substituting an amino group for the hydroxyl residue normally present at the terminal carboxyl group of a peptide. That is, instead of a terminal COOH, the peptides were synthesized to have CO—NH$_2$. For example, preferred small peptides include glycyl-lysyl-glycine amide (GKG-NH$_2$), cystyl-glutaminyl-glycine amide (CQG-NH$_2$), glycyl-prolyl-glycine amide (GPG-NH$_2$), arginyl-glutaminyl-glycine amide (RQG-NH$_2$), lysyl-glutaminyl-glycine amide (KQG-NH$_2$), alanyl-leucyl-glycine amide (ALG-NH$_2$), glycyl-valyl-glycine amide (GVG-NH$_2$), valyl-glycyl-glycine amide (VGG-NH$_2$), alanyl-seryl-glycine amide (ASG-NH$_2$), seryl-leucyl-glycine amide (SLG-NH$_2$), and seryl-prolyl-threonine amide (SPT-NH$_2$). In addition to those synthesized, many tripeptides were also purchased from Bachem AG, Switzerland, including but not limited to, GKG-NH$_2$, CQG-NH$_2$, and GPG-NH$_2$.

In the toxicology experiments and experiments that evaluated the effects of small peptide treatment in combination with conventional antiviral therapies, the peptides were obtained as follows. For the initial experiments, solid phase peptide synthesis was performed using an Applied Biosystems 430A peptide synthesizer (Applied Biosystems, Foster City, Calif.). Each synthesis used a p-methylbenzylhydrylamine solid phase support resin (Peptide International, Louisville, Ky.) yielding a carboxyl terminal amide when the peptides are cleaved off from the solid support by acid hydrolysis. All amino acids for use in synthesis contained t-butylcarbonyl groups protecting the α-NH2 group and were obtained from Novabiochem AG, Switzerland. The protecting groups were removed from the synthesized peptides that were cleaved from the solid support resin by treatment with trifluoromethane sulfonic acid, giving peptides with an amino (—NH2) modulation group instead of a hydroxyl (—OH) group at the carboxyl terminus. Prior to use, the peptides were purified by reverse phase high performance liquid chromatography and sequenced on an Applied Biosystems 473A peptide sequencer. In addition, the tripeptide GPG having either an amide (CO—NH$_2$; GPG-NH2) or carboxyl (COOH; GPG-OH) terminus was purchased from Bachem AG, Switzerland.

In the disclosure below, several assays that were used to identify small peptides that inhibit HIV-1, HIV-2, and SIV infection are described.

HIV and SIV Infectivity Assays

The peptides made according to Example 1 were used in several HIV-1, HIV-2, and SIV infection assays. The efficiency of HIV-1, HIV-2, and SIV infection was monitored by reverse transcriptase activity, the concentration of p24 protein in the cell supematent, and by microscopic evaluation of HIV-1 syncytia formation.

In initial experiments, several tripeptides were screened for the ability to inhibit HIV-1, HIV-2, and SIV infection in H9 cells. Once inhibitory tripeptides were identified, more specific assays were conducted to determine the effect of varying concentrations of the selected tripeptides and combination treatments (e.g., the use of more than one tripeptide in combination).

In the example below, an approach that was used to screen several tripeptides for their ability to inhibit HIV-1, HIV-2, and SIV infection is disclosed.

EXAMPLE 2

In this example, the methods that were used to analyze the ability of various tripeptides to inhibit HIV-1, HIV-2, and SIV replication are disclosed. In Experiments 1 and 2, approximately 200,000 H9 cells were infected with HIV-1, HIV-2 or SIV at 25 TCID$_{50}$ to test the inhibitory effect of the following synthesized tripeptides LKA-NH$_2$, ILK-NH$_2$, GPQ-NH$_2$, GHK-NH$_2$, GKG-NH$_2$, ACQ-NH$_2$, CQG-NH$_2$, ARV-NH$_2$, KAR-NH$_2$, HKA-NH$_2$, GAT-NH$_2$, KAL-NH$_2$, and GPG-NH$_2$. Accordingly, the H9 cells were resuspended with or without the different peptides (approximately 100 µM) in 1 ml of RPMI 1640 medium supplemented with 10% (v/v) heat-inactivated fetal bovine serum (FBS), penicillin (100 u/ml), and streptomycin (100 u/ml), all available through GIBCO, and Polybrene (2 µg/ml), available through Sigma. Thereafter, viruses were added at 25 TCID$_{50}$ in a volume of 20–30 µl. Cells were incubated with virus at 37° C. for 1 hr then pelleted at 170×g for 7 minutes. The cells were then washed three times in RPMI medium without peptides at room temperature and pelleted at 170×g for 7 minutes, as above. After the final wash, the cells were resuspended in RPMI culture medium containing the peptides in a 24-well plate (Costar corporation) and were kept at 37° C. in 5% CO$_2$ with humidity.

Culture supernatants were collected and analyzed when the medium was changed at 4, 7, 10, and 14 days post infection. To monitor the replication of virus, reverse transcriptase (RT) activity in the supernatants was assayed using a commercially available Lenti-RT activity kit. (Cavidi Tech, Uppsala, Sweden). The amount of RT was determined with the aid of a regression line of standards. The results are presented as absorbance values (OD) and higher absorbance indicates a higher protein concentration and greater viral infection. Syncytium formation was also monitored by microscopic examination. Tables 2 and 3 show the absorbance values of the cell culture supernatants of Experiments 1 and 2 respectively.

In Experiment 3, (Table 4), approximately 200,000 H9 cells were infected with HIV-1, HIV-2 or SIV at 25 $TCID_{50}$ to test the inhibitory effect of different concentrations of peptides $GPG-NH_2$, $GKG-NH_2$ and $CQG-NH_2$ and combinations of these peptides (the indicated concentration corresponds to the concentration of each tripeptide). As above, H9 cells were resuspended with or without the different peptides at varying concentrations in 1 ml of RPMI 1640 medium supplemented with 10% (v/v) heat-inactivated fetal bovine serum (FBS), penicillin (100 u/ml), and streptomycin (100 u/ml), and Polybrene (2 $\mu$g/ml). Thereafter, viruses were added at 25 $TCID_{50}$ in a volume of 20–30 $\mu$l. Cells were incubated with the indicated virus at 37° C. for 1 hr then pelleted at 170×g for 7 minutes. The cells were then washed three times in RPMI medium without peptides at room temperature and pelleted at 170×g for 7 minutes, as above. After the final wash, the cells were resuspended in RPMI culture medium containing the peptides in a 24-well plate (Costar corporation) and kept at 37° C. in 5% $CO_2$ with humidity.

Culture supernatants were collected when the medium was changed at 4, 7, and 11 days post infection. As above, the replication of each virus was monitored by detecting reverse transcriptase (RT) activity in the supernatants using the Lenti-RT activity kit. (Cavidi Tech). The amount of RT was determined with the aid of a regression line of standards. The results are presented as absorbance values (OD) and higher absorbance indicates a higher protein concentration and greater viral infection. Table 4 shows the absorbance values of the cell culture supernatents of Experiment 3.

In Experiment 4, (Table 5) approximately 200,000 H9 cells were infected with HIV-1 at 25 $TCID_{50}$ to test the inhibitory effect of different concentrations of peptides $GPG-NH_2$, $GKG-NH_2$ and $CQG-NH_2$ and combinations of these peptides (the indicated concentration corresponds to the total concentration of tripeptide). As above, H9 cells were resuspended with or without the different peptides at varying concentrations in 1 ml of RPMI 1640 medium supplemented with 10% (v/v) heat-inactivated fetal bovine serum (FBS), penicillin (100 u/ml), and streptomycin (100 u/ml), and Polybrene (2 $\mu$g/ml). Thereafter, viruses were added at 25 $TCID_{50}$ in a volume of 20–30 $\mu$l. Cells were incubated with the indicated virus at 37° C. for 1 hr then pelleted at 170×g for 7 minutes. The cells were then washed three times in RPMI medium without peptides at room temperature and pelleted at 170×g for 7 minutes, as above. After the final wash, the cells were resuspended in RPMI culture medium containing the peptides in a 24-well plate (Costar corporation) and kept at 37° C. in 5% $CO_2$ with humidity.

Culture supernatants were collected when the medium was changed at 4, 7, and 11 days post infection. As above, the replication of each virus was monitored by detecting reverse transcriptase (RT) activity in the supernatants using the Lenti-RT activity kit. (Cavidi Tech). The amount of RT was determined with the aid of a regression line of standards. The results are presented as absorbance values (OD) and higher absorbance indicates a higher protein concentration and greater viral infection. Table 5 shows the absorbance values of the cell culture supernatents of Experiment 4. The supernatant analyzed at day 11 was diluted 5-fold so that detection could be more accurately determined.

In Experiment 5, (Table 6) approximately 200,000 H9 cells were infected with HIV-1 at 25 $TCID_{50}$ to test the inhibitory effect of different concentrations of peptides $GPG-NH_2$, $GKG-NH_2$ and $CQG-NH_2$ and combinations of these peptides. As above, H9 cells were resuspended with or without the different peptides at varying concentrations in 1 ml of RPMI 1640 medium supplemented with 10% (v/v) heat-inactivated fetal bovine serum (FBS), penicillin (100 u/ml), streptomycin (100 u/ml), and Polybrene (2 $\mu$g/ml). Thereafter, viruses were added at 25 $TCID_{50}$ in a volume of 20–30 $\mu$l. Cells were incubated with the indicated virus at 37° C. for 1 hr then pelleted at 170×g for 7 minutes. The cells were then washed three times in RPMI medium without peptides at room temperature and pelleted at 170×g for 7 minutes, as above. After the final wash, the cells were resuspended in RPMI culture medium containing the peptides in a 24-well plate (Costar corporation) and kept at 37° C. in 5% $CO_2$ with humidity.

Culture supernatants were collected when the medium was changed at 4, 7, and 14 days post infection. The replication of each virus was monitored by detecting the presence of p24 in the supernatants. HIV p24 antigen was determined using a commercially available HIV p24 antigen detection kit (Abbott). The results are presented as absorbance values (OD) and higher absorbance indicates a higher protein concentration and greater viral infection. In some cases, serial dilutions of the supernatants were made so as to more accurately detect p24 concentration. Table 6 shows the absorbance values of the cell culture supernatants of Experiment 5. As discussed in greater detail below, it was discovered that the tripeptides $GPG-NH_2$, $GKG-NH_2$ and $CQG-NH_2$ and combinations of these peptides effectively inhibit HIV-1, HIV-2, and SIV infection.

In experiment 6 (Table 7 and FIG. 1), approximately 200,000 HUT78 cells were infected with HIV-1 at 25 $TCID_{50}$ to test the inhibitory effect of $GPG-NH_2$, $RQG-NH_2$, $KQG-NH_2$, $ALG-NH_2$, $GVG-NH_2$, $VGG-NH_2$, $ASG-NH_2$, $SLG-NH_2$, and $SPT-NH_2$. The HUT cells were resuspended in 1 ml of RPMI 1640 medium supplemented with 10% (v/v) heat-inactivated fetal bovine serum (FBS, GIBCO), penicillin (100 u/ml), streptomycin (100 u/ml) and Polybrene (Sigma, 2 $\mu$g/ml) with or without the presence of the different small peptides (100 $\mu$M) mentioned above. Thereafter, the HIV-1 virus was added at 25 $TCID_{50}$ in a volume of 20 $\mu$l. Cells were incubated with the virus at 37° C. for one hour and, subsequently, the cells were pelleted at 170×g for seven minutes. The cells were then washed three times in RPMI medium without peptides at room temperature by cell sedimentation at 170×g for seven minutes, as above. After the final wash, the cells were resuspended in RPMI culture medium containing the peptides in 24-well plate (Costar corporation) and were kept at 37° C. in 5% $CO_2$ with humidity. Culture supernatants were collected when medium was changed at day 4, 7, and 11 post infection and viral p24 production was monitored by using an HIV-1 p24 ELISA kit (Abbott Laboratories, North Chicago, USA). As discussed below, it was discovered that the small peptides $RQG-NH_2$, $KQG-NH_2$, $ALG-NH_2$, $GVG-NH_2$, $VGG-NH_2$, $ASG-NH_2$, $SLG-NH_2$, and $SPT-NH_2$ effectively inhibit HIV-1 infection.

TABLE 2

Experiment 1 - (peptides made on site)

| Tripeptide (100 μM) | Day 7 RT | | | Day 10 RT | | | HIV-1 Syncytia |
|---|---|---|---|---|---|---|---|
| | HIV-1 | HIV-2 | SIV | HIV-1 | HIV-2 | SIV | |
| LKA-NH$_2$ | 0.568* | 3.649 | 3.577 | 2.429 | 2.769 | 2.452 | pos |
| ILK-NH$_2$ | 0.365 | 3.467 | 3.180 | 2.033 | 2.791 | 2.255 | pos |
| GPQ-NH$_2$ | 0.204 | 3.692 | 1.542 | 1.965 | 2.734 | 2.176 | pos |
| GHK-NH$_2$ | 0.289 | 3.522 | 0.097 | 2.151 | 2.931 | 2.384 | pos |
| GKG-NH$_2$ | 0.080 | 0.160 | 0.421 | 0.074 | 0.147 | 0.099 | neg |
| ACQ-NH$_2$ | 0.117 | 3.418 | 1.241 | 0.904 | 2.753 | 2.746 | pos |
| CQG-NH$_2$ | 0.091 | 0.217 | 0.747 | 0.108 | 0.296 | 0.110 | neg |
| ARV-NH$_2$ | 0.156 | 3.380 | 0.210 | 1.528 | 3.003 | 1.172 | pos |
| KAR-NH$_2$ | 0.380 | 3.419 | 0.266 | 2.779 | 2.640 | 1.722 | pos |
| HKA-NH$_2$ | 0.312 | 3.408 | 0.416 | 2.546 | 2.669 | 2.520 | pos |
| GAT-NH$_2$ | 0.116 | 3.461 | 0.892 | 1.565 | 2.835 | 2.343 | pos |
| KAL-NH$_2$ | 0.246 | 3.372 | 1.091 | 1.995 | 2.749 | 2.524 | pos |
| GPG-NH$_2$ | 0.068 | 0.735 | 0.138 | 0.074 | 0.145 | 0.103 | neg |
| NO PEPTIDE CONTROL | 0.251 | 1.675 | 1.227 | 2.217 | 2.657 | 3.030 | pos |

*Values represent opitcal density (OD)

TABLE 3

Experiment 2 - (peptides made on site)

| Tripeptide (100 μM) | Day 7 RT | | | Day 10 RT | | | HIV-1 Syncytia |
|---|---|---|---|---|---|---|---|
| | HIV-1 | HIV-2 | SIV | HIV-1 | HIV-2 | SIV | |
| LKA-NH$_2$ | 0.894* | 1.689 | 0.724 | 2.989 | 2.637 | 2.797 | pos |
| ILK-NH$_2$ | 0.581 | 1.692 | 0.515 | 2.950 | 2.557 | 2.632 | pos |
| GPQ-NH$_2$ | 0.884 | 1.511 | 0.574 | 2.848 | 2.382 | 2.319 | pos |
| GHK-NH$_2$ | 0.829 | 1.936 | 0.396 | 3.013 | 2.418 | 2.394 | pos |
| GKG-NH$_2$ | 0.145 | 0.283 | 0.116 | 0.345 | 1.637 | 0.204 | neg |
| ACQ-NH$_2$ | 0.606 | 1.661 | 0.612 | 2.831 | 2.505 | 2.606 | pos |
| CQG-NH$_2$ | 0.143 | 1.241 | 0.120 | 1.546 | 2.501 | 1.761 | neg |
| ARV-NH$_2$ | 0.618 | 2.237 | 0.212 | 2.829 | 2.628 | 3.004 | pos |
| KAR-NH$_2$ | 0.753 | 1.904 | 1.034 | 2.928 | 2.742 | 2.672 | pos |
| HKA-NH$_2$ | 1.081 | 1.678 | 0.455 | 2.794 | 2.560 | 2.623 | pos |
| GAT-NH$_2$ | 0.776 | 1.707 | 0.572 | 2.800 | 2.565 | 2.776 | pos |
| KAL-NH$_2$ | 0.999 | 1.757 | 0.511 | 2.791 | 2.383 | 2.663 | pos |
| GPG-NH$_2$ | 0.090 | 0.093 | 0.067 | 0.143 | 0.575 | 0.139 | neg |
| NO PEPTIDE CONTROL | 0.809 | 1.774 | 0.578 | 2.711 | 2.528 | 2.911 | pos |

*Values represent opitcal density (OD)

TABLE 4

Experiment 3 - (peptides obtained from Bachem)

| Tripeptide | Day 7 RT | | | Day 10 RT | | |
|---|---|---|---|---|---|---|
| | HIV-1 | HIV-2 | SIV | HIV-1 | HIV-2 | SIV |
| NO PEPTIDE CONTROL | 1.558* | 1.718 | 1.527 | 2.521 | 2.716 | 2.091 |
| GPG-NH$_2$ 5 μM | 1.527 | 1.735 | 0.753 | 2.398 | 2.329 | 2.201 |
| GPG-NH$_2$ 20 μM | 0.239 | 0.252 | 0.197 | 0.692 | 1.305 | 0.779 |
| GKG-NH$_2$ 5 μM | 1.587 | 1.769 | 0.271 | 1.683 | 2.510 | 1.709 |

TABLE 4-continued

Experiment 3 - (peptides obtained from Bachem)

| Tripeptide | Day 7 RT | | | Day 10 RT | | |
|---|---|---|---|---|---|---|
| | HIV-1 | HIV-2 | SIV | HIV-1 | HIV-2 | SIV |
| GKG-NH$_2$ 20 μM | 1.616 | 1.759 | 1.531 | 2.036 | 2.646 | 2.482 |
| GKG-NH$_2$ 100 μM | 0.823 | 0.828 | 1.005 | 1.520 | 1.947 | 1.382 |
| CQG-NH$_2$ 5 μM | 1.547 | 1.760 | 1.159 | 2.028 | 2.466 | 2.821 |
| CQG-NH$_2$ 20 μM | 1.578 | 1.748 | 0.615 | 1.484 | 2.721 | 2.158 |
| CQG-NH$_2$ 100 μM | 1.520 | 1.715 | 0.795 | 2.014 | 2.815 | 2.286 |
| GPG-NH$_2$ + GKG-NH$_2$ 5 μM | 1.430 | 1.738 | 1.131 | 1.998 | 2.770 | 2.131 |
| GPG-NH$_2$ + GKG-NH$_2$ 20 μM | 0.129 | 0.244 | 0.123 | 0.164 | 1.110 | 0.309 |
| GPG-NH$_2$ + CQG-NH$_2$ 5 μM | 1.605 | 1.749 | 1.737 | 1.866 | 2.814 | 2.206 |
| GPG-NH$_2$ + CQG-NH$_2$ 20 μM | 0.212 | 0.194 | 0.523 | 0.397 | 1.172 | 0.910 |
| GKG-NH$_2$ + CQG-NH$_2$ 5 μM | 1.684 | 1.717 | 1.725 | 1.848 | 2.778 | 2.949 |
| GKG-NH$_2$ + CQG-NH$_2$ 20 μM | 1.490 | 1.792 | 1.670 | 1.891 | 2.799 | 2.889 |
| GPG-NH$_2$ + GKG-NH$_2$ 5 μM | 1.652 | 1.743 | 1.628 | 1.999 | 2.777 | 2.659 |
| GPG-NH$_2$ + GKG-NH$_2$ 20 μM | 0.165 | 0.119 | 0.317 | 0.307 | 0.447 | 0.389 |

*Values represent opitcal density (OD)

TABLE 5

Experiment 4 - (peptides obtained from Bachem)

| Tripeptide | Day 7 RT HIV-1 | Day 10 RT HIV-1 (1:5) |
|---|---|---|
| NO PEPTIDE CONTROL | 3.288* | 1.681 |
| GPG    5 μM | 2.970 | 1.107 |
| GPG   15 μM | 0.894 | 0.095 |
| GPG   45 μM | 0.177 | 0.034 |
| GPG  100 μM | 0.150 | 0.033 |
| GKG    5 μM | 3.303 | 1.287 |
| GKG   15 μM | 3.551 | 1.530 |
| GKG   45 μM | 3.126 | 0.410 |
| CQG    5 μM | 2.991 | 1.459 |
| CQG   15 μM | 2.726 | 1.413 |
| CQG   45 μM | 3.124 | 1.364 |
| GPG-NH$_2$ + GKG-NH$_2$ 5 μM | 2.266 | 0.438 |
| GPG-NH$_2$ + GKG-NH$_2$ 15 μM | 0.216 | 0.044 |
| GPG-NH$_2$ + CQG-NH$_2$ 5 μM | 2.793 | 0.752 |
| GPG-NH$_2$ + CQG-NH$_2$ 15 μM | 0.934 | 0.110 |
| GKG-NH$_2$ + CQG-NH$_2$ 5 μM | 3.534 | 1.305 |
| GKG-NH$_2$ + CQG-NH$_2$ 15 μM | 3.355 | 2.013 |
| GPG-NH$_2$ + GKG-NH$_2$ + CQG-NH$_2$ 5 μM | 2.005 | 0.545 |
| GPG-NH$_2$ + GKG-NH$_2$ + CQG-NH$_2$ 15 μM | 0.851 | 0.110 |

*Values represent optical density (OD)

TABLE 6

Experiment 5 - (peptides made on site)

| Tripeptide (μM) | p24 (OD) | p24 (pg/ml) | reduction (%) |
|---|---|---|---|
| HIV-I | | | |
| Day 7 | | | |
| NO PEPTIDE CONTROL | 1.093 × 10$^2$ | 3.94 × 10$^4$ | 0 |
| GPG-NH$_2$   (20) | 1.159 | 4.21 × 10$^2$ | 99 |
| GPG-NH$_2$   (100) | 0.508 | 1.60 × 10$^2$ | 100 |
| GPG-NH$_2$   (300) | 0.557 | 1.80 × 10$^2$ | 100 |
| GKG-NH$_2$   (100) | 0.566 × 10$^1$ | 1.83 × 10$^3$ | 95 |
| GKG-NH$_2$   (300) | 1.08 | 3.88 × 10$^2$ | 99 |
| GKG-NH$_2$  (1000) | 0.79 | 2.73 × 10$^2$ | 100 |
| CQG-NH$_2$   (100) | 1.51 × 10$^1$ | 5.62 × 10$^3$ | 86 |
| CQG-NH$_2$   (300) | 0.59 × 10$^1$ | 1.92 × 10$^3$ | 95 |
| CQG-NH$_2$  (1000) | 0.91 | 3.20 × 10$^2$ | 99 |
| combined* | 0.65 | 2.17 × 10$^2$ | 100 |
| Day 14 | | | |
| NO PEPTIDE CONTROL | 0.46 × 10$^4$ | 1.41 × 10$^6$ | 0 |
| GPG-NH$_2$   (20) | 1.12 × 10$^2$ | 4.06 × 10$^4$ | 97 |
| GPG-NH$_2$   (100) | 1.76 | 6.63 × 10$^2$ | 100 |
| GPG-NH$_2$   (300) | 1.35 | 4.98 × 10$^2$ | 100 |
| GKG-NH$_2$   (100) | 1.48 × 10$^3$ | 5.51 × 10$^5$ | 61 |
| GKG-NH$_2$   (300) | 0.33 × 10$^1$ | 8.70 × 10$^2$ | 100 |
| GKG-NH$_2$  (1000) | 0.11 × 10$^1$ | 2.40 × 10$^2$ | 100 |
| CQG-NH$_2$   (100) | 0.48 × 10$^4$ | 1.47 × 10$^6$ | 0 |
| CQG-NH$_2$   (300) | 0.11 × 10$^2$ | 2.40 × 10$^3$ | 100 |
| CQG-NH$_2$  (1000) | 0.13 × 10$^1$ | 2.80 × 10$^2$ | 100 |
| combined* | 1.01 | 3.61 × 10$^2$ | 100 |

*100 μM GPG - NH$_2$ + GKG - NH$_2$ + CQG - NH$_2$
*Values represent opitcal density (OD)

TABLE 7

Experiment 6 - (peptides made on site)

| Tripeptide (100 μM)<br>Day 7 HIV-1 | p24 (pg/ml) | reduction (%) |
|---|---|---|
| NO PEPTIDE CONTROL | $2.0 \times 10^4$ | 0 |
| GPG-NH$_2$ | $5.6 \times 10^2$ | 97 |
| RQG-NH$_2$ | $1.13 \times 10^2$ | 99 |
| KQG-NH$_2$ | $1.54 \times 10^2$ | 99 |
| ALG-NH$_2$ | $0.42 \times 10^2$ | 100 |
| GVG-NH$_2$ | $1.5 \times 10^4$ | 25 |
| VGG-NH$_2$ | $1.0 \times 10^4$ | 50 |
| ASG-NH$_2$ | $1.5 \times 10^4$ | 25 |
| SLG-NH$_2$ | $1.14 \times 10^2$ | 99 |
| SPT-NH$_2$ | $1.5 \times 10^4$ | 25 |

Small Peptides Inhibit and/or Prevent HIV-1, HIV-2, and SIV Infection

Of the small peptides listed in Table 1, GPG-NH$_2$, GKG-NH$_2$, CQG-NH$_2$, RQG-NH$_2$, KQG-NH$_2$, ALG-NH$_2$, GVG-NH$_2$, VGG-NH$_2$, ASG-NH$_2$, SLG-NH$_2$, and SPT-NH$_2$ inhibited and/or prevented HIV-1 infection and GKG-NH$_2$, CQG-NH$_2$, and GPG-NH$_2$ were also shown to inhibit or prevent HIV-2 and SIV infection. It should be understood that the small peptides RQG-NH$_2$, KQG-NH$_2$, ALG-NH$_2$, GVG-NH$_2$, VGG-NH$_2$, ASG-NH$_2$, SLG-NH$_2$, and SPT-NH$_2$ were not analyzed for their ability to prevent or inhibit HIV-2 or SIV infection but, given the fact that HIV-2 and SIV share significant homology in capsid protein structure at the region to which the small peptides GPG-NH$_2$, GKG-NH$_2$, CQG-NH$_2$, RQG-NH$_2$, KQG-NH$_2$, ALG-NH$_2$, GVG-NH$_2$, VGG-NH$_2$, ASG-NH$_2$, SLG-NH$_2$, and SPT-NH$_2$ correspond, an inhibition or prevention of HIV-2 or SIV infection or both is expected.

The results for Experiments 1–6 (shown in Tables 2–7 and FIG. 1), demonstrate that small peptides in amide form that correspond to viral capsid protein sequence having a glycine as the carboxyterminal amino acid, GPG-NH$_2$, GKG-NH$_2$, CQG-NH$_2$, RQG-NH$_2$, KQG-NH$_2$, ALG-NH$_2$, GVG-NH$_2$, VGG-NH$_2$, ASG-NH$_2$, and SLG-NH$_2$, inhibited or prevented HIV infection. Peptides containing a carboxyterminal alanine residue, Leu-Lys-Ala (LKA) and His-Lys-Ala (HKA) or a carboxyterminal glutamine residue, Gly-Pro-Gln (GPQ) and Ala-Cys-Gln (ACQ) did not prevent HIV infection. Glycine at the amino terminus was not an inhibitory factor, however, because the peptides with an amino terminal glycine residue, Gly-Pro-Gln (GPQ), Gly-His-Lys (GHK), and Gly-Ala-Thr (GAT) failed to prevent infection and HIV-1 syncytia formation. Further, peptides with other uncharged polar side chains such as Gly-Pro-Gln (GPQ), Ala-Cys-Gln (ACQ), and Gly-Ala-Thr (GAT) or non-polar side chains at the carboxy terminus such as Ala-Arg-Val (ARV), His-Lys-Ala (HKA), and Lys-Ala-Leu (KAL), and Leu-Lys-Ala (LKA) failed to prevent infection. Although a glycine residue at the carboxy terminus appears to be associated with the inhibition of HIV and SIV infection, other amino acid residues or modified amino acid residues at the carboxy terminus of a small peptide can also inhibit HIV and SIV infection. For example, it was shown that Ser-Pro-Thr (SPT) inhibited or prevented HIV-1 infection.

In some experiments it appeared that the effect of the small peptides on HIV-1, HIV-2, and SIV infection was concentration and time dependent. Concentrations of GKG-NH$_2$, CQG-NH$_2$, and GPG-NH$_2$ and combinations thereof, as low as 5 μM and 20 μM were shown to be effective at reducing HIV-1, HIV-2, and SIV infection. At 100 μM or greater, however, the tripeptides GKG-NH$_2$, CQG-NH$_2$, and GPG-NH$_2$ and combinations thereof more efficiently inhibited HIV-1, HIV-2, and SIV infection. As shown in Table 6, 300 μM of GKG-NH2 and CQG-NH2 reduced HIV-1 infectivity by almost 100%, as detected by the presence of p24 antigen in cell supernatents. The percent reduction tabulated in Table 6 was calculated by dividing amount of p24 antigen detected in the peptide-treated sample by the amount of p24 antigen detected in the control sample, multiplying this dividend by 100 to obtain a percentage, and subtracting the dividend percentage by 100%. For example, the percent reduction exhibited by GPG-NH$_2$ is:

$$\frac{5.6 \times 10^2}{2.0 \times 10^4} \times 100 = 3\% \text{ and } 100\% - 3\% = 97\%.$$

In the first five experiments (Tables 2–6) it was shown that the tripeptides GKG-NH$_2$, CQG-NH$_2$, and GPG-NH$_2$ and combinations thereof, inhibit HIV-1, HIV-2, and SIV infection at concentrations equal to or greater than 5 μM.

In the sixth experiment (Table 7 and FIG. 1), it was shown that the small peptides RQG-NH$_2$, KQG-NH$_2$, ALG-NH$_2$, GVG-NH$_2$, VGG-NH$_2$, ASG-NH$_2$, SLG-NH$_2$, and SPT-NH$_2$ effectively inhibit and/or prevent HIV-1 infection at 100 μM. As shown in Table 7, a nearly 100% reduction of virus, as measured by the amount of capsid protein p24 in the supernatent, was achieved with the small peptides RQG-NH$_2$, KQG-NH$_2$, ALG-NH$_2$, and SLG-NH$_2$. The percent reduction of p24 shown in Table 7 was calculated as described for Table 6, above. Although GVG-NH$_2$, VGG-NH$_2$, ASG-NH$_2$, and SPT-NH$_2$ were less effective at inhibiting or preventing HIV-1 infection at 100 μM, it is believed that the tripeptides are more effective at higher concentrations. The data presented in experiments 1–6, shown in Tables 2–7 and FIG. 1, demonstrate that small peptides that correspond to sequences of a viral capsid protein are effective antiviral agents over a wide-range of concentrations.

In order to better understand small peptide-mediated viral inhibition, several studies on DNA synthesis, RNA synthesis, and protein expression were conducted. These experiments are discussed below.

Small Peptides Inhibit Viral Infectivity at a Stage Subsequent to DNA Synthesis, RNA Synthesis, and Protein Expression To study proviral DNA and viral RNA synthesis, DNA and RNA from HIV-1 infected H-9 cells cultured in the presence of a small peptide were prepared at various time points (0–48 h). Southern blot analysis revealed that HIV-1 DNA was synthesized in the presence of GPG-NH$_2$ and the amount of proviral DNA was almost equal at various concentrations (0–2,000 μM) of the small peptide during the first 24 h. These results prove that small peptides, such as GPG-NH$_2$, have no inhibitory effect on HIV-1 entry and DNA synthesis, and coincide with the finding that the small peptides do not inhibit HIV-1 reverse transcriptase activity.

By Northern blot analysis, three RNA bands (9.2, 4.3, 2.0 kb) were detected 24–48 h after infection. The 9.2 kb RNA acts as both the genomic RNA and as the mRNA for the gag and pol genes. The 4.3 kb singly-spliced RNA represents at least the env gene, and the multiply-spliced 2 kb RNA encodes for the regulatory genes. GPG-NH$_2$ at 20 μM had no inhibitory effect on expression of these RNAs up to 48 h post infection. At 200 μM and 2,000 μM a reduction of HIV-1 RNA was noticed 48 h after infection that probably reflects inhibition of the second replication cycle. These results established that small peptides do not inhibit HIV-1 replication at the transcription step, nor do they affect the splicing of transcripts.

In the experiments designed to determine whether HIV-1 properly expresses protein in the presence of small peptides, no significant effect on protein expression or modification was observed. In one experiment, however, an aberrant migration of gp160/gp120 on a polyacrylamide gel was seen. In the presence GPG-NH$_2$ (20 µM or more), gp160 and/or gp120 was observed to electrophorese to a position on a polyacrylamide gel representative of a molecular weight of slightly less than 120,000 Da. This result was not reproducible and a change in migration of the gag-proteins p17 or p24 was not observed. Studies to analyze glycosylation of the virus protein in the presence of GPG-NH$_2$ showed that there was no effect on either N- or O-linked glycosylation. Also, glycosylation on recombinantly (in vaccinia virus) produced gp160 was not affected by GPG-NH$_2$. Furthermore, GPG-NH$_2$ was found not to affect the activity of the HIV-1 specific protease.

In the experiments presented above, it was demonstrated that small peptides interfere with HIV infectivity at a late stage of the HIV replicative cycle. GPG-NH$_2$ was unable to disrupt DNA synthesis, RNA synthesis, protein synthesis, and protein glycosylation. In the following disclosure, more evidence that small peptides, such as GPG-NH$_2$, GKG-NH$_2$, CQG-NH$_2$, RQG-NH$_2$, KQG-NH$_2$, ALG-NH$_2$, GVG-NH$_2$, VGG-NH$_2$, ASG-NH$_2$, SLG-NH$_2$, and SPT-NH$_2$, inhibit viral infection at a late stage in the replicative cycle is disclosed and, in a broader sense, another technique that can be used to screen other small peptides and derivatives thereof for the ability to inhibit viral infection, such as HIV or SIV infection, is provided. Accordingly, discussed below are several electron microscopy experiments in which HIV-1 infected cells were incubated in the presence and absence of a small peptide.

Small Peptides Interfere with Assembly of the Nucleocapsid

Figure 2:
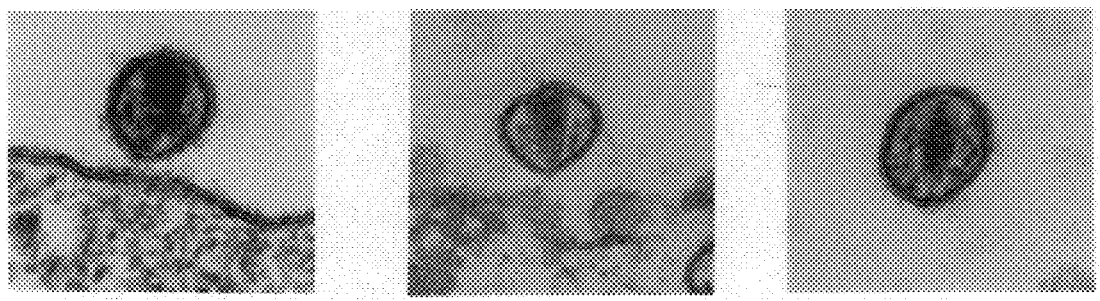
FIG. 2 is a composite of electron micrographs of untreated HIV particles.
Figure 4:
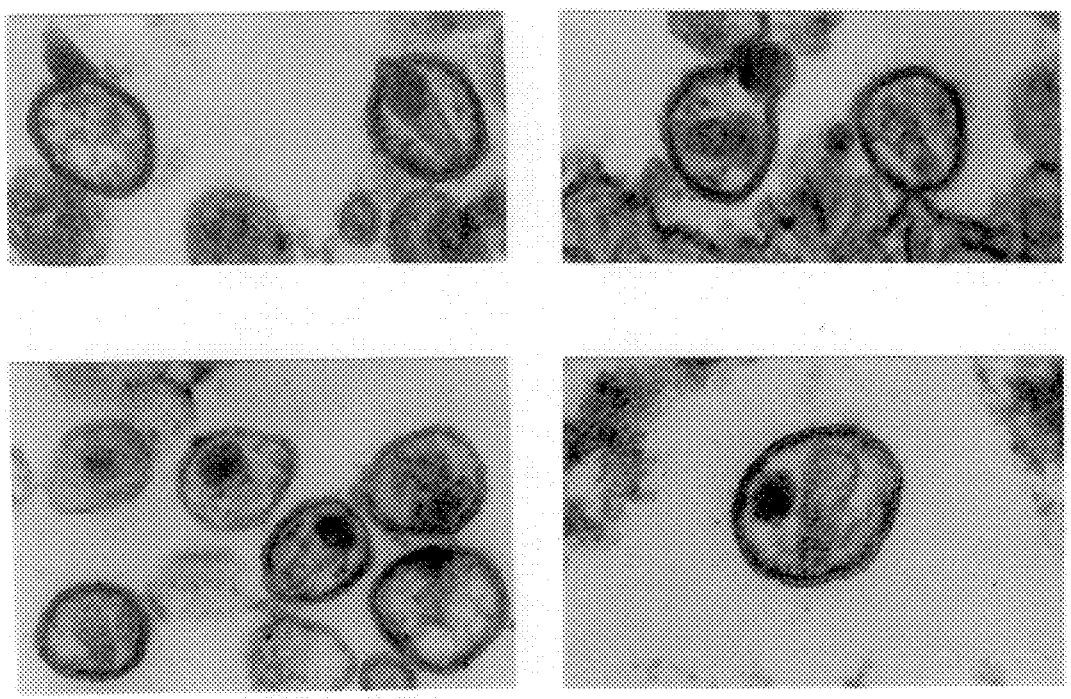
FIG. 4 is a composite of electron micrographs of HIV particles that have been contacted with GPG-$NH_2$.

Once it had been discovered that the small peptides GPG-NH$_2$, GKG-NH$_2$, CQG-NH$_2$, RQG-NH$_2$, KQG-NH$_2$, ALG-NH$_2$, GVG-NH$_2$, VGG-NH$_2$, ASG-NH$_2$, SLG-NH$_2$, and SPT-NH$_2$ inhibited HIV infection, electron microscopy was used to further analyze HIV infected cells that had been incubated with a small peptide. (See FIGS. 2, 3, and 4). As shown in FIG. 4, electron microscopic analysis revealed that contact with GPG-NH$_2$ interrupted proper viral nucleocapsid formation.

In this set of experiments, HUT78 cells were infected with HIV-1 SF-2 virus at 300TCID$_{50}$ for 1 hr at 37° C. Subsequently, the infected cells were washed and pelleted 3 times, as described in Example 2. Thereafter, the cells were resuspended in RPMI culture medium supplemented with 10% FBS, antibiotics (100 u/ml) and polybrene (3.2 µg/ml). GPG-NH$_2$ was then added into the cell cultures 3, 5 or 7 days post infection at concentration of 1 µM or 10 µM. A control sample was administered 0.5 µM Ritonavir (a protease inhibitor).

The cells were cultured until day 14, at which point, the cells were fixed in 2.5% glutaraldehyde by conventional means. The fixed cells were then postfixed in 1% OsO$_4$ and were dehydrated, embedded with epoxy resins, and the blocks were allowed to polymerize. Epon sections of virus infected cells were made approximately 60–80 nm thin in order to accommodate the width of the nucleocapsid. The sections were mounted to grids stained with 1.0% uranyl acetate and were analyzed in a Zeiss CEM 902 microscope at an accelerating voltage of 80 kV. The microscope was equipped with a spectrometer to improve image quality and a liquid nitrogen cooling trap was used to reduce beam damage. The grids having sections of control and GPG-NH$_2$ incubated cells were examined in several blind studies.

Electron microscopy of untreated HIV particles revealed the characteristic conical-shaped nucleocapsid and enclosed uniformly stained RNA that stretched the length of the nucleocapsid. (See FIG. 2). In contrast, FIG. 3 presents two electron micrographs showing several HIV-1 particles that were produced in the presence of the viral protease inhibitor Ritonavir. Infected cells that had been treated with Ritonavir exhibited malformed structures that did not have a discernable nucleocapsid, as was expected. (See FIG. 3). FIG. 4 presents electron micrographs showing viral particles that had been produced in the presence of GPG-NH$_2$. Cells having HIV-1 particles that were treated with GPG-NH$_2$ exhibited HIV-1 particles with discernable capsid structures that are distinct from the Ritonavir-treated particles. More specifically, in some tripeptide-treated viral particles, the conical-shaped capsid structure appeared to be relatively intact but the RNA was amassed in a ball-like configuration either outside the capsid or at the top (wide-end) of the capsid. Still further, some capsids were observed to have misshapen structures with little or no morphology resembling a normal nucleocapsid and RNA was seen to be either outside the structure or inside the structure at one end. From these studies it was clear that small peptides interfered with proper formation of the nucleocapsid and that this inhibition of capsid development occurred at a step distinct from the action of the protease inhibitor Ritonavir.

More evidence that tripeptides in amide form, such as GPG-NH$_2$, GKG-NH$_2$, CQG-NH$_2$, RQG-NH$_2$, KQG-NH$_2$, ALG-NH$_2$, GVG-NH$_2$, VGG-NH$_2$, ASG-NH$_2$, SLG-NH$_2$, and SPT-NH$_2$, interfere with capsid assembly was revealed when a binding assay with p24 as a target biomolecule was performed. The details of the p24 binding assay are provided below.

Small Peptides Bind to the Major Capsid Protein (p24)

Experiments were performed to directly study whether small peptides have the ability to interact with the mature capsid protein (CA) or p24 and thereby interfere with nucleocapsid formation. In this set of experiments, a p24 binding assay was performed that assessed the ability of radiolabeled GPG-NH$_2$ to bind to p24.

A dialysis-based binding assay was conducted using a dialysis membrane with a pore size of less than 10 kD. (Slide-A-Lyzer, Pierce). Fifty microliters of a 10 µM stock of the recombinant proteins p24 and gp120 (gifts from the AIDS program, NCIB) and BSA (Sigma) were introduced into separate dialysis membranes and the proteins were dialyzed at 4° C. for 2 days against a 500 ml solution composed of 150 mM NaCl and 50 mM Tris-HCl, pH 7.4 buffer and 27.5 µM of $^{14}$C-GPG-NH$_2$ (Amersham Ltd. UK). Subsequently, ten or five microliter aliquots of the dialyzed p24, gp120, and BSA were removed and mixed with 3 ml of ReadySafe (Beckman) in a scintillation vial. The C$^{14}$ was then detected by scintillation counting.

In Table 8, the results from a representative dialysis experiment are provided. Notably, an association of p24 with GPG-NH$_2$ was observed upon dialysis equilibration. The amount of radioactive GPG-NH$_2$ associated with p24 was 7.5 times greater than that present in the buffer. In contrast, no appreciable amount of radioactive GPG-NH$_2$, over the amount present in the dialysis buffer, was associated with either gp120 or BSA. These results prove that small peptides, such as GPG-NH$_2$, bind to p24 and through this interaction interupt proper nucleocapsid formation.

TABLE 8

| Sample: | dialysis buffer | p24 | gp120 | BSA |
|---|---|---|---|---|
| µ Ci/ml | 1.816 | 13.712 | 1.745 | 1.674 |
| times buffer | 1.000 | 7.551 | 0.961 | 0.922 |

In the following disclosure, additional evidence that small peptides, such as GPG-NH$_2$, GKG-NH$_2$, CQG-NH$_2$, RQG- NH$_2$, KQG-NH$_2$, ALG-NH$_2$, GVG-NH$_2$, VGG-NH$_2$, ASG-NH$_2$, SLG-NH$_2$, and SPT-NH$_2$, inhibit HIV and SIV infection by a mechanism that is different from the way that AZT or Ritonavir inhibit these viruses is provided.

Small Peptides Inhibit HIV-1 Strains that are Resistant to AZT or Ritonavir

The ability of small peptides to inhibit HIV-1 strains that are resistant to either the nucleoside analogue AZT or the protease inhibitor Ritonavir. The HIV-1 resistant isolates were cultivated in peripheral blood mononuclear cells (PBMC) and the supernatants were collected as virus stocks. Titration of $TCID_{50}$ (50% tissue culture infectious dose) were performed on PBMC and the titers were calculated according to the Reed and Muench formula. 400,000 PBMC were infected with 25 $TCID_{50}$ of those viruses (HIV-1 SF162 was used as a control) by adsorption in 37° C. for one hour then washed three times. The cells were resuspended in culture medium containing either no drug, GPG-$NH_2$ (100 $\mu$M), AZT (5 $\mu$M), or Ritonavir (0.1 $\mu$M) and incubated in 37° C., $CO_2$ and humidity. Culture medium was changed every four days and the HIV-1 p24 antigen protein in the supernatants was monitored by ELISA (Table 9).

As shown in Table 9, GPG-$NH_2$ had a potent anti-viral effect on either AZT or Ritonavir resistant HIV strains. The results in this experiment substantiate the data presented above and prove that small peptides inhibit HIV replication at a different stage than AZT and Ritonavir. Additionally, the treatment of "street strains" of HIV was accomplished with GPG-$NH_2$, as disclosed in U.S. Pat. No. 5,627,035 to Vahlne et al., herein incorporated by reference in its entirety. Given that they are also derived from the sequence of the HIV viral protein, the peptides GKG-$NH_2$, CQG-$NH_2$, RQG-$NH_2$, KQG-$NH_2$, ALG-$NH_2$, GVG-$NH_2$, VGG-$NH_2$, ASG-$NH_2$, SLG-$NH_2$, and SPT-$NH_2$ are also useful in the treatment of AZT and Ritonavir resistant HIV infections, as well as street strains of HIV.

TABLE 9

| Types | Number | Control (%) | GPG 100 $\mu$M (% reduction) | AZT 5 $\mu$M (% reduction) | Rito[b] 0.1 $\mu$M (% reduction) |
|---|---|---|---|---|---|
| low AZT | p7261 | 130000* (0) | <500 (100%) | <500 (100%) | nt |
| inter AZT | p7163 | 107000 (0) | <500 (100%) | 22200 (79%) | nt |
| high AZT | p7227 | 114000 (0) | <500 (100%) | 68000 (40%) | nt |
| low PI | p7300 | 146000 (0) | <500 (100%) | nt[a] | 64000 (56%) |
| high PI | p7141 | 114000 (0) | <500 (100%) | nt | 98000 (14%) |

*HIV-1 p24 values are shown in pg/ml and are averages of duplicate experiments taken 14 days post infection.
[a]not tested
[b]Ritonavir
Low AZT: isolated with a low resistance to AZT.
Inter AZT: isolated with a intermediate resistance to AZT.
High AZT: isolated with a high resistance to AZT.
Low PI: isolated with a low resistance to protease inhibitor.
High PI: isolated with a high resistance to protease inhibitor.

In further support of the data presented above, several HIV-1 infectivity experiments on an HIV-1 mutant that lacked the GPG-motif in its V3 loop were performed. These experiments, detailed below, established that GPG-$NH_2$-mediated HIV-1 inhibition occurs in a V3 loop independent fashion. The V3 loop of HIV-1 env glycoprotein gp120 contains a conserved GPG sequence at the tip of the loop that may be involved in virus replication. To determine whether GPG-$NH_2$ inhibited HIV-1 infection by perturbing a V3 loop interaction, a V3 loop HIV-1 mutant provirus was constructed. This mutant provirus lacking the GPG domain was tested for its ability to infect cells in infectivity assays and was analyzed by immunocytochemistry and electron microscopy. The example below describes the construction of the mutant provirus, the assay for HIV-1 infectivity, the determination of the structure of the mutant viral particles by immunocytochemistry and electron microscopy, and the discovery that GPG-$NH_2$ inhibits the infection by mutant viral particles.

EXAMPLE 3

A GPG-deleted provirus based on the infectious clone pBRu-2 was constructed using conventional techniques in molecular biology. *Escherichia coli* DH5α and NM522 mutS were used for sub-cloning, mutagenesis, and amplification of plasmid DNAs. The puc18 plasmid was used as a vector for sub-cloning, and the HIV-1 proviral clone pBRu-2, which contains a full-length, replication-competent clone of HIV-1/Bru (also designated as LAV, LAI), was used to generate mutant virus.

The 2.7-kb SalI-to-BamHI fragment from pBRu-2, which encodes the env gene, was sub-cloned into the SalI and BamHI sites of the puc18 vector. GPG deletion was accomplished by site-directed mutagenesis using the U.S.E. Mutagenesis Kit (Pharmacia). Two oligonucleotides were required. The mutagenic oligonucleotide was 5'phosphorylated CGT ATC CAG AGG AGA GCA TTT GTT ACA ATA GG-3' (obtained from Scandinavian Gene Synthesis AB, Stockholm, Sweden). The selective oligonucleotide was 5'-phosphorylated GTG CCA CCT GTC GAC TAA GAA ACC AT-3' and was designed to remove a unique restriction site, AatII, in the puc18 vector. The wild-type DNA was, thus, selectively eliminated from the mixed pool of wild-type and mutant DNA by digestion with the corresponding endonuclease AatII. The mutagenesis reaction products were transformed into *E. coli* to amplify the plasmid DNAs. The mutation was verified by Polymerase Chain Reaction (PCR) sequencing of the DNA using an Automated Laser Fluorescent ALF™ DNA Sequencer (Pharmacia). The SalI-BamHI fragment deleted from the oligonucleotide encoding GPG was then cloned into pBRu-2 to generate the proviral plasmid. The mutant DNAs from several bacterial colonies were amplified and purified by QIAGEN Plasmid Kit. Two of them, mp8 and mp10 DNAs, were transfected into cells.

The wild-type DNA and the mutant DNA, mp8 and mp10 were transfected into Hela, $HUT_{78}$, or MT-2 cells using DEAE-dextran method. (Palker et al., *Proc. Natl. Acad. Sci. USA* 85: 1932–1936 (1988)). Briefly, $10^6$ cells were prepared 24 hours before transfection. Then, the medium was removed and the cells were washed once with pre-warmed phosphate-buffered-saline (PBS) and once with TBS-D (Tris buffered saline-0.1% dextrose). Approximately 0.5 $\mu$g DNA was mixed with TBS-D/DEAE-dextran and was added to the cells followed by a 30 minute-incubation at 37° C. Then the solution was removed and the cells were washed once with TBS-D and once with PBS. The cells were mixed with 5 ml pre-warmed medium supplemented with 10% serum and 5 $\mu$g chloroquine diphosphate and were incubated 1 hour at 37° C. followed by three times washes with serum-free medium. Finally, the cells were maintained in 10 ml culture medium and incubated at 37° C. for 4 days.

Virus-containing supernatants were collected, filtered through a 0.45 $\mu$g pore-size filter to remove any cells, aliquoted and kept at −70° C. as virus stock. Titration of virus was performed by infecting MT-2 cells with serial dilutions of virus. One hundred microliters from each five-fold serial dilution of the virus supernatants served as inoculum for 200,000 MT 2 cells. After 16 hours adsorption, the cells were washed five times and resuspended in 1.5 ml culture medium in 24-well plates (Costar Corporation). Medium was changed at 4, 7, and 11 days post infection and p24 production in the supernatants was tested on day 14. The 50% tissue culture infectious dose ($TCID_{50}$) end point was calculated according to the Reed-Muench formula. (Reed and Muench, Am. J. Hygiene 27: 493–497 (1938)).

CD4+T-cell lines MT-2, C91-PL, C8166, CEM, $HUT_{78}$, H9, Jurkat and Molt-3, monocytic cell lines U937, and THP-1, were propagated and maintained in RPMI1640 medium (GIBCO) supplemented with 10% (v/v) heat-inactivated fetal bovine serum (GIBCO), penicillin (100 u/ml) and streptomycin (100 u/ml). Hela cells were grown in medium 199 with Hank's salt supplemented with 2% FBS, 0.8% dextrose and antibiotics.

Peripheral blood mononuclear cells (PBMCs) were purified by Ficoll-Hypaque density gradient centrifugation and stimulated with phytohemagglutinin (KEBO Lab) for three days in RPMI 1640 medium supplemented as described above before being infected. Dendritic cells (DCs) were generated from blood monocytes that were purified from the mononuclear fraction by adherence to plastic as described by Rormani et al., J. Exp. Med. 180:83–93 (1994). In brief, blood mononuclear cells were purified, as described above, and adherence was carried out onto tissue-culture flasks in RPMI medium for two hours, then the non-adherent cells were washed away with PBS. The adherent cells were cultured for seven days in medium with GM-CSF (25 u/ml) and IL-4 (4.5 u/ml) and then were infected with virus.

Infections were performed on cell-lines MT-2, C9 1-PL, C8166, CEM, $HUT_{78}$, H9, Jurkat, Molt-3, U937, THP-1, PBMCs and dendritic cells (DCs). For CD4+ cell-lines, 200,000 cells were incubated in 37° C. with wild-type or mutant virus at 100 $TCID_{50}$ for 16 hours, then washed five times, resuspended in 1.5 ml fresh RPMI medium supplemented with 10% FBS, antibiotics and Polybrene (Sigma, 2 µg/ml) and incubated in 24-well plate in 37° C. in 5% $CO_2$ with humidity. For PBMCs, 500,000 cells were used and cultured in RPMI medium supplemented with proleukin (Eurocetus, 150 u/ml), hydrocortisone (Sigma, 5 µg/ml) and polybrene (Sigma, 2 µg/ml). For DCs, 800,000 cells were exposed to virus for 1, 16 and 48 hours, respectively followed by 3 times of wash in PBS and gentle treatment of 0.05% trypsin in 37° C. for 5 minutes to remove any surface-bound virus, as described by Grannelli-Piperno et al, J. Exp. Med. 184:2433–2438 (1996). As a control, PBMCs were exposed to mp8 in the same way. The cells were washed, collected and lysed to isolate DNAs by phenol/chloroform extraction then a semi-quantitative PCR detecting LTR sequence was performed. Ten-fold serial dilutions were made on the DNAs and the LTR PCR was performed in a 40 cycles, using a three primer "nested" configuration as described before. (Hwang et al., Science 253: 71–74 (1991)). For DC-PBMC co-culture and DC-MT-2 co-culture experiments, 250,000 DCs were exposed to virus for 16 hours followed by five times of washes until no p24 could be detected (less than 5 µg/ml). Then the cells were gently treated with 0.05% trypsin that destroys the HIV-1 binding epitope on CD4 and removes any surface-bound virus. After washing, the cells were resuspended in RPMI culture medium mixed with 200,000 PBMCs cells or 100,000 MT-2 cells.

For infection experiments, culture medium was changed at 4, 7, 11, 14 and 17 days post infection and viral growth was determined by p24 levels using an HIV-1 p24 ELISA kit (Abbott Laboratories, North Chicago, USA). The ELISA quantitation of the p24 assay was used to quantitate the level of p24 in each virus sample and this assay had a linear dose-response range from 20 µg to 640 µg of p24 per ml. All virus samples were assayed at multiple dilutions and p24 amount was determined with the aid of a regression line. DNAs were isolated from the cells cultured for 17 days post infection and direct sequencing of the V3 region was performed on these DNAs to verify the mutation.

Immunocytochemistry was also performed on infected and uninfected MT-2 cells by an APAAP (Alkaline Phosphatase Anti-Alkaline Phosphatase immunocomplexes) sandwich technique as previously described in Kowalski et al., Science 237:1351–1355 (1987). Cells were washed twice in PBS and fixed on slides by acetone for 15 minutes. Then the cells were incubated in succession with the primary antibody mouse anti-HIV-1 p24, the secondary antibody rabbit anti-mouse immunoglobulins, and mouse APAAP monoclonal antibody (DAKO) for 30 minutes at 37° C., respectively, in a humid chamber followed by washing in PBS for 5 minutes. After chromogenic substrate was added and incubated for 20 minutes at room temperature, slides were washed in $H_2O$, mounted in glycerol and viewed under microscopy (magnification x100). The monoclonal antibodies (Mabs) mouse anti-HIV-1 p24 (DAKO, diluted 1:20), rabbit anti-mouse immunoglobulins (diluted 1:25) and mouse immunocomplexes of Mab to calf intestinal alkaline phosphatase and calf intestinal alkaline phosphatase (APAAP, diluted 1:20) were used for the immunocytochemistry assay.

Additionally, electron microscopy was performed on infected cells. Freshly infected cells were fixed on day 7 by 2.5% glutaraldehyde and postfixed in 1% OSO4. The cells were dehydrated, embedded with epoxy resins and stained with 1% uranyl acetate. Epon sections of virus infected cells were made 60–80 nm thin. The specimens were analyzed in a Zeiss CEM 902 at an accelerating voltage of 80 kV, which was equipped with a spectrometer to improve image quality. A liquid nitrogen cooling trap was used to reduce beam damage.

In another set of experiments, more evidence that GPG-$NH_2$ inhibits HIV-1 infection by a mechanism other than V3 loop inhibition was obtained. Accordingly, the ability of GPG-$NH_2$ to inhibit the infectivity of wild-type and V3-loop deletion mutants (GPG domain) in MT-2 cells was determined. In these experiments, approximately 200,000 MT-2 cells were infected with HIV-$1_{Bru}$ wild-type and GPG-deleted mutants mp8 and mp10 at 25 $TCID_{50}$ to test the inhibitory effect of GPG-$NH_2$ The MT-2 cells were resuspended in 1 ml of RPMT 1640 medium supplemented with 10% (v/v) heat-inactivated fetal bovine serum (FBS, GIBCO), penicillin (100 µ/ml), streptomycin (100 µ/ml) and Polybrene (Sigma 2 µg/ml) with or without the presence of GPG-$NH_2$ at concentration 20 of µM and 100 µM. Thereafter, viruses were added at 25 $TCID_{50}$ in a volume of 20–30 µl. Cells were incubated with virus at 37° C. for 16 hr then loosely pelleted by centrifugation at 170xg for 7 minutes. The cells were then washed three times in RPMI medium without peptides at room temperature by cell sedimentation at 170xg for 7 minutes as above. After the final wash, the cells were resuspended in RPMI culture medium in 24-well plate (Costar corporation) then kept at 37° C. in 5% $CO_2$ with humidity. Culture supernatants were collected when medium was changed at day 4, 7, 11 and 14 post infection. To monitor the replication of virus, HIV-1 p24 antigen protein in the supernatants from day 7 and 14 was assayed by a ELISA kit (Abbott Laboratories) which has a linear dose-response range from 20 pg to 640 pg of p24 per ml and the p24 amount can be determined with aid of the regression line.

The results from the experiments described in this example, discussed in greater detail below, verify that GPG-NH$_2$ inhibits HIV-1 infection in a V3 loop independent manner.

Small Peptides Inhibit HIV-1 Infection in a V3 Loop Independent Manner

To determine if the GPG-deletion in the V3 loop affected the production of virus, the proviral plasmid DNAs (both wild-type and mutant) were transfected into the CD4 negative cell line Hela, as well as, the CD4 positive cell lines MT-2 and HUT$_{78}$. Culture supernatants were collected every day and virus production was monitored by measuring p24 levels. A similar growth pattern was observed for the wild-type virus (WT) and the mutants from Hela transfections, within a 6-day time frame. The p24 levels kept increasing until day 4, then stayed on a plateau. Hence, both the mutant and the wild-type proviral DNAs were equally well expressed in these cells. Similar results were obtained from HUT$_{78}$, transfectants and syncytia were observed in these transfected HUT$_{78}$ cells. The pattern of p24 production from MT-2 transfections, however, were notably different from those observed in Hela and HUT78 cells. The p24 product level kept increasing beyond day four although the p24 production of cells transfected with the mutant virus proviral DNAs were lower than those transfected with the wild-type virus proviral DNA. On day 6 post transfection, the wild-type produced 1,380 ng/ml of p24 while the p24 production of mp8 and mp10 were 15.8 ng/ml and 13.7 ng/ml, respectively. These results demonstrate that GPG-deleted mutant progeny viruses were produced and could infect non-transfected CD4+MT-2 cells, albeit apparently not as efficiently as did wild-type progeny. DNAs from these transfected cells were sequenced and the GPG deletion was verified for both the mp8 and the mp10 progeny.

Next, the ability of the mutant molecular clones to generate virus particles capable of establishing an infection was further analyzed. Hela cells and MT-2 cells were transfected with the proviral DNAs and four days post transfection the culture supernatants were collected, filtered, assayed for p24 levels and aliquots were frozen at −70° C. as virus stocks. Viral titration (TCID$_{50}$) was performed on MT-2 cells. Supernatants from MT-2 transfectants, adjusted to contain the same amount of p24, the wild-type virus yielded 83,300 TCID$_{50}$/ml whereas the mutants, mp8 and mp10 yielded 16,700 and 25,000 TCID$_{50}$/ml, respectively—about five fold less than what was obtained with the wild-type virus. In concordance with a lower p24 production of the Hela transfectant supernatants, the titers they yielded were also much lower, 70 and 10 TCID$_{50}$/ml for WT and mutants respectively. Thus, although the mutant virus was still infectious, deletion of the GPG motif in V3 may have reduced the viral virulence in these cells. This was further tested by infection of MT-2 cells and monitored the production of progeny virus. The virus stocks from both Hela and MT-2 transfections were then used to infect MT-2 cells (100 TCID$_{50}$ wild type or mutant virus from MT-2 transfectant supernatants, or five TCID$_{50}$ of Virus from Hela transfectant stocks). The cells were incubated with virus for 16 hours and then washed. Thereafter, the cells were resuspended and incubated at 37° C. Virus replication was monitored by measuring p24 levels and cytopathic effects. With virus from MT-2 transfectants, wild-type (WT), as well as, the mutant virus (mp8 and mp10), all showed viral replication by p24 production. Wild-type reached peak p24 levels of 2,150 ng/ml at day 11 post infection while the mutant viruses exhibited approximately a 4-day delay, with peak p24 values of 1,580 ng/ml and 1,760 ng/ml for mp8 and mp10, respectively at day 14 post infection. Infections of MT-2 cells with virus from Hela transfectants (at 5 TCID$_{50}$) also yielded p24 production of both the WT and the mutants with similar growth kinetics as those obtained with MT-2 cell produced virus. DNAs were isolated from all infected cells and the mutation was verified by V3 sequencing, indicating that the growth of the mutant virus was not due to reversion to or pick up of the wild-type sequence.

Syncytium formation was also observed in the MT-2 cells infected with both the WT and the mutants. Cell cultures were fixed at day 7 post infection and was used for immunocytochemistry using the APAAP sandwich technique. The infected cells were immunostained and gave a red color. Syncytia were observed in both WT and mutant virus infected MT-2 cells, although WT virus induced syncytia earlier (4 days post infection) than the mutants (after 6 days). Electron microscopy (EM) further revealed that the mutant virus infected MT-2 cells produced HIV-1 particles. HIV-1 particles, having a characteristic cone-shaped core, were seen. These data confirmed that the GPG-deletion mutant virus remained infectious in MT-2 cells.

Conclusive evidence that GPG-NH2 inhibits viral infection by a mechanism different than a V3 loop interaction was obtained when experiments that assessed the ability of GPG-NH$_2$ to inhibit the infectivity of wild-type and V3-loop deletion mutants (GPG domain) in MT-2 cells were performed. At both 7 days and 14 days after infection, a considerable reduction in wild type and mutant viral infection was seen. See Table 10. At 20 $\mu$M and 100 $\mu$M, GPG-NH$_2$ effectively reduced reduced wild type infection and infection mediated by the GPG deletion constructs mp8 and mp10. In fact, at 7 days post infection and 100 $\mu$M GPG-NH2, an equally complete reduction of viral infectivity was observed for wild-type, mp8, and mp10. These results established that GPG-NH2 was inhibiting HIV-1 infection by a mechanism independent from an interaction with the GPG domain of the V3 loop.

TABLE 10

| | p24 pg/ml control | GPG 20 $\mu$M | reduction % | GPG 100 $\mu$M | reduction % |
| --- | --- | --- | --- | --- | --- |
| Day 7 | | | | | |
| WT | 33800 | 23900 | 29 | 3390 | 90 |
| mp 8 | 3170 | 2420 | 24 | 208 | 93 |
| mp 10 | 3120 | 1560 | 50 | 173 | 94 |
| Day 14 | | | | | |
| WT | 357000 | 223000 | 38 | 181000 | 49 |
| mp 8 | 148000 | 69100 | 53 | 7410 | 95 |
| mp 10 | 470000 | 51500 | 89 | 47700 | 90 |

The data presented herein establish that small peptides having a modified carboxy terminus inhibit viral infection (e.g., HIV-1, HIV-2, and SIV infection), bind to p24, and interrupt proper capsid assembly. The many assays detailed above can be used to identify the ability of any small peptide, modified small peptide, oligopeptide, or peptidomimetic to prevent or inhibit HIV or SIV infection. Similar techniques can also be used to identify the ability of any small peptide, modified small peptide, oligopeptide, or peptidomimetic to prevent or inhibit other viral infections.

Because the sequence of several viral capsid proteins are known, the design, manufacture, and identification of small peptides in amide form that prevent proper assembly of different viral capsids is straightforward. Several viral capsid proteins, for instance, contain a 20 amino acid long homology region called the major homology region (MHR), that exists within the carboxyl-terminal domain of many onco- and lentiviruses. (See FIG. 5). FIG. 5 shows the carboxyl-terminal domain of HIV-1 (residues 146–231) and compares this sequence to the capsid protein sequences of other viruses, some of which infect birds, mice, and monkeys. Notably, considerable homology in the sequences of these viral capsid proteins is found. Investigators have observed that the carboxyl-terminal domain is required for capsid dimerization and viral assembly in HIV-1. (Gamble et al., *Science* 278: 849 (1997), herein incorporated by reference in its entirety). While the small peptides that exhibited antiviral activity in the assays described in this disclosure fully or partially corresponded to regions of the carboxyl-terminal domain of HIV-1, HIV-2, or SIV, regions of the N-terminal domain of viruses are important for capsid assembly and the design and synthesis of small peptides that either fully or partially correspond to amino acids of the N-terminal region of viral capsid proteins are desirable embodiments of the present invention. The use of small peptides that fully or partially correspond to amino acids within the MHR region and the carboxyl-terminal domain of viral capsid proteins, however, are preferred embodiments of the present invention.

The inventor has shown several novel small peptides in amide form that fully or partially correspond to to capsid protein sequence of three different viruses effectively inhibit and/or prevent infection by these viruses. The strategies employed herein can be used to produce additional small peptides in amide form that fully or partially correspond to the capsid protein sequences of other viruses. By designing and manufacturing small peptides, oligopeptides, and/or peptidomimetics that correspond to regions of the sequences disclosed in FIG. 5, for example, new molecules that inhibit HIV, SIV, RSV, HTLV-1, MMTV, MPMV, and MMLV infection can be rapidly identified by using the screening techniques discussed above or modifications of these assays, as would be apparent to one of skill in the art. Further, many of the sequences of other viral capsid proteins are known, such as members of the arenavirus, rotavirus, orbivirus, retrovirus, papillomavirus, adenovirus, herpesvirus, paramyxovirus, myxovirus, and hepadnavirus families. Several small peptides, oligopeptides, and/or peptidomimetics that fully or partially correspond to these sequences can be selected and rapidly screened to identify those that effectively inhibit and/or prevent viral infection by using the viral infectivity assays and/or electron microscopy techniques described herein, or modifications of these assays as would be apparent to those of skill in the art given the present disclosure.

Desirable embodiments include small peptides (more than one amino acid and less than or equal to 10 amino acids in length) having a modified carboxy terminus that are used to interrupt capsid assembly and inhibit viral infection. Preferably, dipeptides, tripeptides, and oligopetides and corresponding peptidomimetics having a sequence that is found in the HIV or SIV capsid are used. For example, an oligopeptide of the present invention may have four amino acids, five amino acids, six amino acids, seven amino acids, eight, or nine or ten amino acids and peptidomimetics of the present invention may have structures that resemble four, five, six, seven, eight, nine, or ten amino acids. These oligopeptides also desirably include the full or partial sequences found in the tripeptides GPG-$NH_2$, GKG-$NH_2$, CQG-$NH_2$, RQG-$NH_2$, KQG-$NH_2$, ALG-$NH_2$, GVG-$NH_2$, VGG-$NH_2$, ASG-$NH_2$, SLG-$NH_2$, and SPT-$NH_2$. Peptidomimetics that resemble dipeptides, tripeptides and oligopeptides also, preferably, correspond to a sequence that is found in GPG-$NH_2$, GKG-$NH_2$, CQG-$NH_2$, RQG-$NH_2$, KQG-$NH_2$, ALG-$NH_2$, GVG-$NH_2$, VGG-$NH_2$, ASG-$NH_2$, SLG-$NH_2$, and SPT-$NH_2$. It is preferred that the small peptides possess a modulation group (e.g., an amide group) at their carboxy termini (CO—$NH_2$) rather than a carboxyl group (COOH). Small peptides having other modulation groups at the carboxy terminus, can also be used but desirably, the attached modulation groups have the same charge and sterically behave the same as an amide group. (See U.S. Pat. No. 5,627,035 to Vahlne et al., for an assay to compare peptides having differing substituents at the carboxyl terminus). In some embodiments, the addition of an acetyl or methyl group at either end of a small peptide is desirable so as to improve uptake of the small peptide or prevent exo-protease digestion or both.

In the following disclosure, several approaches are provided to make biotechnological tools and pharmaceutical compositions comprising dipeptides, tripeptides, oligopeptides of less than or equal to 10 amino acids, and peptidomimetics that resemble tripeptides and oligopeptides of less than or equal to 10 amino acids (collectively referred to as a "peptide agent(s)"). It should be noted that the term "peptide agents" includes dipeptides, tripeptides, and oligopeptides of less than equal to 10 amino acids. "Peptide agents" are, for example, peptides of two, three, four, five, six, seven, eight, nine, or ten amino acids and peptidomimetics that resemble peptides of two, three, four, five, six, seven, eight, nine, or ten amino acids. Further, "peptide agents" are peptides of two, three, four, five, six, seven, eight, nine, or ten amino acids or peptidomimetics that resemble two, three, four, five, six, seven, eight, nine, or ten amino acids that are provided as multimeric or multimerized agents, as described below.

Desirable biotechnological tools or components to prophylactic or therapeutic agents, provide the peptide agent in such a form or in such a way that a sufficient affinity or inhibition of a virus, such as HIV-1, HIV-2, or SIV, is obtained. While a natural monomeric peptide agent (e.g., appearing as discrete units of the peptide agent each carrying only one binding epitope) is sufficient to bind a capsomere protein, such as p24, and/or interfere with capsid assembly and/or prevent viral infection, such as HIV-1, HIV-2, or SIV infection, synthetic ligands or multimeric ligands (e.g., appearing as multiple units of the peptide agent with several binding epitopes) may have far greater ability to bind a capsomere protein, such as p24, and/or interfere with capsid assembly and/or prevent viral infection, such as HIV-1, HIV-2, or SIV infection. It should be noted that the term "multimeric" is meant to refer to the presence of more than one unit of a ligand, for example several individual molecules of a tripeptide, oligopeptide, or a peptidomimetic, as distinguished from the term "multimerized" that refers to the presence of more than one ligand joined as a single discrete unit, for example several tripeptides, oligopeptides, or peptidomimetic molecules joined in tandem.

Preparation of Multimeric Supports and Multimerized Ligands

A multimeric agent (synthetic or natural) that binds a capsomere protein, such as p24, and/or interferes with capsid assembly and/or inhibits viral infection, such as HIV-1, HIV-2, or SIV infection, may be obtained by coupling a tripeptide, oligopeptide or a peptidomimetic to a macromolecular support. The term "support" as used herein includes a carrier, a resin or any macromolecular structure used to attach, immobilize, or stabilize a peptide agent. Solid supports include, but are not limited to, the walls of wells of a reaction tray, test tubes, polystyrene beads, magnetic beads, nitrocellulose strips, membranes, microparticles such as latex particles, sheep (or other animal) red blood cells, artificial cells and others. The term Support also includes carriers as that term is understood for the preparation of pharmaceuticals.

The macromolecular support may have a hydrophobic surface that interacts with a portion of the peptide agent by hydrophobic non-covalent interaction. The hydrophobic surface of the support may also be a polymer such as plastic or any other polymer in which hydrophobic groups have been linked such as polystyrene, polyethylene or polyvinyl. Alternatively, the peptide agent can be covalently bound to carriers including proteins and oligo/polysaccharides (e.g. cellulose, starch, glycogen, chitosane or aminated sepharose). In these later embodiments, a reactive group on the peptide agent, such as a hydroxy or an amino group, may be used to join to a reactive group on the carrier so as to create the covalent bond. The support may also have a charged surface that interacts with the peptide agent. Additionally, the support may have other reactive groups that can be chemically activated so as to attach a peptide agent. For example, cyanogen bromide activated matrices, epoxy activated matrices, thio and thiopropyl gels, nitrophenyl chloroformate and N-hydroxy succinimide chlorformate linkages, and oxirane acrylic supports are common in the art.

The support may also comprise an inorganic carrier such as silicon oxide material (e.g. silica gel, zeolite, diatomaceous earth or aminated glass) to which the peptide agent is covalently linked through a hydroxy, carboxy or amino group and a reactive group on the carrier. Furthermore, in some embodiments, a liposome or lipid bilayer (natural or synthetic) is contemplated as a support and peptide agents are attached to the membrane surface or are incorporated into the membrane by techniques in liposome engineering. By one approach, liposome multimeric supports comprise a peptide agent that is exposed on the surface of the bilayer and a second domain that anchors the peptide agent to the lipid bilayer. The anchor may be constructed of hydrophobic amino acid residues, resembling known transmembrane domains, or may comprise ceramides that are attached to the first domain by conventional techniques.

Supports or carriers for use in the body, (i.e. for prophylactic or therapeutic applications) are desirably physiological, non-toxic and preferably, non-immunoresponsive. Contemplated carriers for use in the body include poly-L-lysine, poly-D, L-alanine, liposomes, and Chromosorbt (Johns-Manville Products, Denver Colo.). Ligand conjugated Chromosorbt (Synsorb-Pk) has been tested in humans for the prevention of hemolytic-uremic syndrome and was reported as not presenting adverse reactions. (Armstrong et al. *J. Infectious Diseases,* 171:1042–1045 (1995)). For some embodiments, the present inventor contemplates the administration of a "naked" carrier (i.e., lacking an attached peptide agent) that has the capacity to attach a peptide agent in the body of a subject. By this approach, a "prodrug-type" therapy is envisioned in which the naked carrier is administered separately from the peptide agent and, once both are in the body of the subject, the carrier and the peptide agent are assembled into a multimeric complex.

The insertion of linkers, such as λ linkers, of an appropriate length between the peptide agent and the support are also contemplated so as to encourage greater flexibility of the peptide agent and thereby overcome any steric hindrance that may be presented by the support. The determination of an appropriate length of linker that allows for optimal binding to a capsomere protein, such as p24, and/or interference with capsid assembly and/or inhibition of viral infection, such as HIV or SIV infection, can be determined by screening the peptide agents with varying linkers in the assays detailed in the present disclosure.

A composite support comprising more than one type of peptide agent is also an embodiment. A "composite support" may be a carrier, a resin, or any macromolecular structure used to attach or immobilize two or more different peptide agents that bind to a capsomere protein, such as p24, and/or interfere with capsid assembly and/or inhibit viral infection, such as HIV or SIV infection. In some embodiments, a liposome or lipid bilayer (natural or synthetic) is contemplated for use in constructing a composite support and peptide agents are attached to the membrane surface or are incorporated into the membrane using techniques in liposome engineering.

As above, the insertion of linkers, such as λ linkers, of an appropriate length between the peptide agent and the support is also contemplated so as to encourage greater flexibility in the molecule and thereby overcome any steric hindrance that may occur. The determination of an appropriate length of linker that allows for optimal binding to a capsomere protein, such as p24, and/or interference with capsid assembly and/or inhibition of viral infection, such as HIV or SIV infection, can be determined by screening the ligands with varying linkers in the assays detailed in the present disclosure.

In other embodiments of the present invention, the multimeric and composite supports discussed above may have attached multimerized ligands so as to create a "multimerized-multimeric support" and a "multimerized-composite support", respectively. A multimerized ligand may, for example, be obtained by coupling two or more peptide agents in tandem using conventional techniques in molecular biology. The multimerized form of the ligand may be advantageous for many applications because of the ability to obtain an agent with a better ability to bind to a capsomere protein, such as p24, and/or interfere with capsid assembly and/or inhibit viral infection, such as HIV or SIV infection. Further, the incorporation of linkers or spacers, such as flexible λ linkers, between the individual domains that make-up the multimerized agent is an advantageous embodiment. The insertion of λ linkers of an appropriate length between protein binding domains, for example, may encourage greater flexibility in the molecule and can overcome steric hindrance. Similarly, the insertion of linkers between the multimerized ligand and the support may encourage greater flexibility and limit steric hindrance presented by the support. The determination of an appropriate length of linker that allows for optimal binding to p24 and/or interference with capsid assembly and/or inhibition of HIV or SIV infection, can be determined by screening the ligands with varying linkers in the assays detailed in this disclosure.

In preferable embodiments, the various types of supports discussed above are created using the tripeptides GPG-$NH_2$, GKG-$NH_2$, CQG-$NH_2$, RQG-$NH_2$, KQG-$NH_2$, ALG-$NH_2$, GVG-$NH_2$, VGG-$NH_2$, ASG-$NH_2$, SLG-$NH_2$, and SPT-$NH_2$. The multimeric supports, composite supports, multimerized-multimeric supports, or multimerized-composite supports, collectively referred to as "support-bound agents", are also preferably constructed using the tripeptides GPG-$NH_2$, GKG-$NH_2$, CQG-$NH_2$, RQG-$NH_2$, KQG-$NH_2$, ALG-$NH_2$, GVG-$NH_2$, VGG-$NH_2$, ASG-$NH_2$, SLG-$NH_2$, and SPT-$NH_2$ In the discussion below, several embodiments of the invention that have therapeutic and/or prophylactic application are described.

Therapeutic and Prophylactic Applications

The monomeric and multimeric peptide agents described herein are suitable for treatment of subjects either as a preventive measure to avoid viral infections, such as HIV or SIV infection, or as a therapeutic to treat subjects already infected with a virus, such as HIV or SIV. Although anyone could be treated with the peptides as a prophylactic, the most suitable subjects are people at risk for viral infection. Such subjects include, but are not limited to, homosexuals, prostitutes, intravenous drug users, hemophiliacs, children born to virus-infected mothers, and those in the medical profession who have contact with patients or biological samples.

The pharmacologically active compounds of this invention can be processed in accordance with conventional methods of galenic pharmacy to produce medicinal agents for administration to patients, e.g., mammals including humans. The peptide agents can be incorporated into a pharmaceutical product with and without modification. Further, the manufacture of pharmaceuticals or therapeutic agents that deliver the peptide agent or a nucleic acid sequence encoding a small peptide by several routes is an embodiment. For example, and not by way of limitation, DNA, RNA, and viral vectors having sequence encoding a small peptide that inhibits viral replication by interupting capsid assembly are contemplated. Nucleic acids encoding a desired peptide agent can be administered alone or in combination with peptide agents.

The compounds described herein can be employed in admixture with conventional excipients, i.e., pharmaceutically acceptable organic or inorganic carrier substances suitable for parenteral, enteral (e.g., oral) or topical application that do not deleteriously react with the peptide agents. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds. They can also be combined where desired with other active agents, e.g., vitamins.

In some embodiments, therapeutic agents comprising peptide agents are administered in conjunction with other therapeutic agents that treat viral infections, such as HIV infection, so as to achieve a better viral response. At present four different classes of drugs are in clinical use in the antiviral treatment of HIV-1 infection in humans. These are (i) nucleoside analogue reverse transcriptase inhibitors (NRTIs), such as zidovidine, lamivudine, stavudine, didanosine, abacavir, and zalcitabine; (ii) nucleotide analogue reverse transcriptase inhibitors, such as adetovir and pivaxir; (iii) non-nucleoside reverse transcriptase inhibitors (NNRTIs), such as efavirenz, nevirapine, and delavirdine; and (iv) protease inhibitors, such as indinavir, nelfinavir, ritonavir, saquinavir and amprenavir. By simultaneously using two, three, or four different classes of drugs in conjunction with administration of the peptide agents, HIV is less likely to develop resistance, since it is less probable that multiple mutations that overcome the different classes of drugs and the peptide agents will appear in the same virus particle.

It is thus a preferred embodiment of the present invention that peptide agents be given in combination with nucleoside analogue reverse transcriptase inhibitors, nucleotide analogue reverse transcriptase inhibitors, non-nucleoside reverse transcriptase inhibitors, and protease inhibitors at doses and by methods known to those of skill in the art. Medicaments comprising the peptide agents and nucleoside analogue reverse transcriptase inhibitors, nucleotide analogue reverse transcriptase inhibitors, non-nucleoside reverse transcriptase inhibitors, and protease inhibitors are also embodiments of the present invention.

Studies on the efficacy of treatment of HIV infection with combinations of $GPG-NH_2$ and conventional antiviral agents can be found in the example provided below.

EXAMPLE 4

Figure 6:
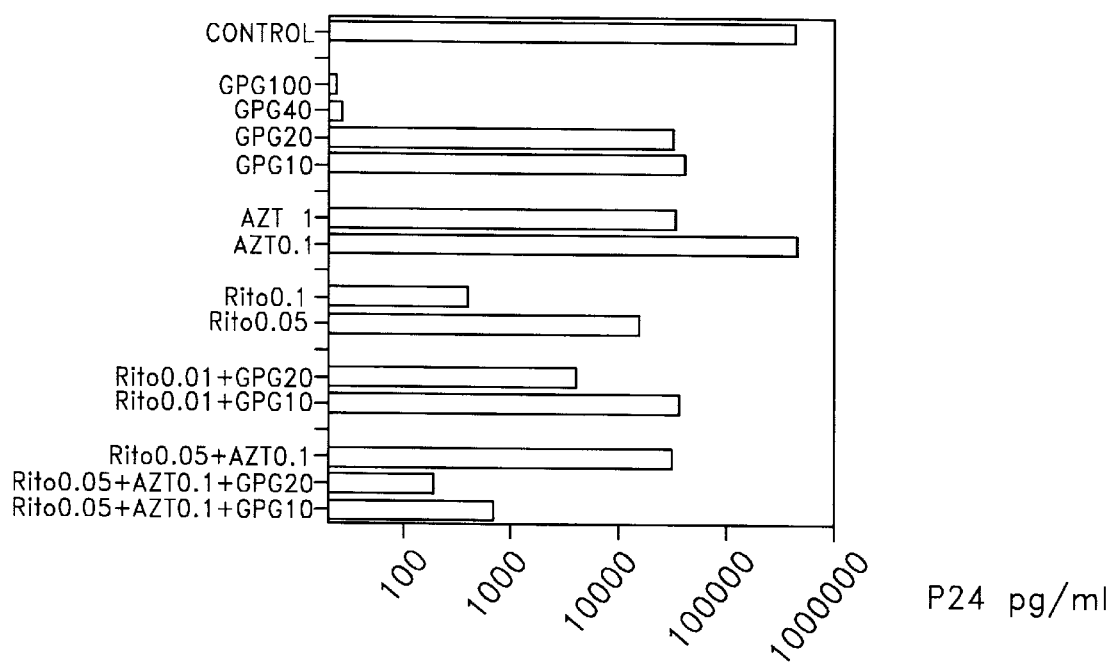
FIG. 6 is a graph of p24 (pg/ml) detected in the supematent of HIV infected cells that were cultured in the presence and absence of GPG-NH2, Ritonavir (Rito), AZT, or combinations of these agents.

In this example, experiments are presented in which different combinations of a small peptide in amide form and AZT were tested to determine whether the two compounds could complement one another to inhibit HIV-1 replication. (See FIG. 6). Accordingly, 200,000 $HUT_{78}$ cells were infected with HIV-1 SF-2 virus at 25 $TCID_{50}$, with or without the presence of different concentrations of $GPG-NH_2$, AZT or Ritonavir ("Rito") and combinations of these compounds. The numbers shown in FIG. 6 represent micromolar concentrations of the inhibiting compounds. Cells were incubated with virus at 37° C. for 1 hr with the various inhibitors and were subsequently washed three times. Next, the cells were resuspended in RPMI 1640 medium containing the antiviral agent and/or the peptides supplemented with 10% (v/v) heat-inactivated fetal bovine serum (FBS, GIBCO), penicillin (100 u/ml), streptomycin (100 u/ml) and Polybrene (Sigma, 2 $\mu$g/ml) and cultured in 24-well plate (Costar corporation) at 37° C. in 5% $CO_2$ with humidity. Culture supernatants were collected every four days and medium was changed until day 14 post infection. To monitor the replication of virus, HIV-1 p24 antigen protein in the supernatants was assayed using a commercially available kit (Abbott).

It was observed that $GPG-NH_2$ enhanced the inhibition of the replication of HIV-1 in the presence of AZT synergistically, whereas, the small peptide only exhibited an additive antiviral effect to that of the protease inhibitor Ritonavir. Nevertheless, these experiments validate data presented above that small peptides inhibit HIV-1 by a mechanism apart from the manner in which nucleoside analogs and protease inhibitors interfere with viral replication. Further, these experiments demonstrate that a novel treatment protocol for HIV-1 infection comprising small peptides and AZT and/or Ritonavir is efficacious.

In the following disclosure, doses and methods of administration are provided.

Dosage and Methods of Administration

The effective dose and method of administration of a particular peptide agent formulation may vary based on the individual patient and the stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Normal dosage amounts may vary from approximately 1 to 100,000 micrograms, up to a total dose of about 10 grams, depending upon the route of administration. Desirable dosages include 250 $\mu$g, 500 $\mu$g, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g. Additionally, the concentrations of the peptide agents can be quite high in embodiments that administer the agents in a topical form. Molar concentrations of peptide agents can be used with some embodiments. Desirable concentrations for topical administration and/or for coating medical equipment range from 100 $\mu$M to 800 mM. Preferable concentrations for these embodiments range from 500 $\mu$M to 500 mM. For example, preferred concentrations for use in topical applications and/or for coating medical equipment include 500 $\mu$M, 550 $\mu$M, 600 $\mu$M, 650 $\mu$M, 700 $\mu$M, 750 $\mu$M, 800 $\mu$M, 850 $\mu$M, 900 $\mu$M, 1 mM, 5 mM, 10 mM, 15 mM, 20 mM, 25 mM, 30 mM, 35 mM, 40 mM, 45 mM, 50 mM, 60 mM, 70 mM, 80 mM, 90 mM, 100 mM, 120 mM, 130 mM, 140 mM, 150 mM, 160 mM, 170 mM, 180 mM, 190 mM, 200 mM, 300 mM, 325 mM, 350 mM, 375 mM, 400 mM, 425 mM, 450 mM, 475 mM, and 500 mM. Guidance as to particular dosages and methods of delivery is provided in the literature, (see e.g., U.S. Pat. Nos. 4,657,760; 5,206,344; or 5,225,212) and below.

More specifically, the dosage of the peptide agents described herein is one that provides sufficient peptide agent to attain a desirable effect including binding of a capsomere protein, such as p24, and/or interference with capsid assembly and/or inhibition of viral infection, such as HIV and SIV infection. Accordingly, the dose of peptide agent preferably produces a tissue or blood concentration or both from approximately 0.1 $\mu$M to 500 mM. Desirable doses produce a tissue or blood concentration or both of about 1 to 800 $\mu$M. Preferable doses produce a tissue or blood concentration of greater than about 10 $\mu$M to about 500 $\mu$M. Preferable doses are, for example, the amount of small peptide required to achieve a tissue or blood concentration or both of 10 $\mu$M, 15 $\mu$M, 20 $\mu$M, 25 $\mu$M, 30 $\mu$M, 35 $\mu$M, 40 $\mu$M, 45 $\mu$M, 50 $\mu$M, 55 $\mu$M, 60 $\mu$M, 65 $\mu$M, 70 $\mu$M, 75 $\mu$M, 80 $\mu$M, 85 $\mu$M, 90 $\mu$M, 95 $\mu$M, 100 $\mu$M, 110 $\mu$M, 120 $\mu$M, 130 $\mu$M, 140 $\mu$M, 145 $\mu$M, 150 $\mu$M, 160 $\mu$M, 170 $\mu$M, 180 $\mu$M, 190 $\mu$M, 200 $\mu$M, 220 $\mu$M, 240 $\mu$M, 250 $\mu$M, 260 $\mu$M, 280 $\mu$M, 300 $\mu$M, 320 $\mu$M, 340 $\mu$M, 360 $\mu$M, 380 $\mu$M, 400 $\mu$M, 420 $\mu$M, 440 $\mu$M, 460 $\mu$M, 480 $\mu$M, and 500 $\mu$M. Although doses that produce a tissue concentration of greater than 800 $\mu$M are not preferred, they can be used with some embodiments of the present invention. A constant infusion of the peptide can also be provided so as to maintain a stable concentration in the tissues as measured by blood levels.

Higher tissue concentrations can be maintained without harm due to the low toxicity of the peptides. Attempts to select small peptide resistant strains of HIV-1 (e.g., GPG-NH$_2$ resistant strains) have so far been unsuccessful. The HIV-1 strain HTLV-IIIB was passaged in the presence of serial dilutions of GPG-NH$_2$ (limiting dilutions) for more than six months without overt signs of development of resistance in vitro.

Routes of administration of the peptide agents include, but are not limited to, topical, transdermal, parenteral, gastrointestinal, transbronchial, and transalveolar. Topical administration is accomplished via a topically applied cream, gel, rinse, etc. containing a peptide. Transdermal administration is accomplished by application of a cream, rinse, gel, etc. capable of allowing the peptide agent to penetrate the skin and enter the blood stream. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions of peptide agent-containing compounds suitable for topical application include, but not limited to, physiologically acceptable implants, ointments, creams, rinses, and gels. Any liquid, gel, or solid, pharmaceutically acceptable base in which the peptides are at least minimally soluble is suitable for topical use in the present invention. Compositions for topical application are particularly useful during sexual intercourse to prevent transmission of HIV. Suitable compositions for such use include, but are not limited to, vaginal or anal suppositories, creams, and douches.

Compositions of the peptide agents suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference and are well known in the art. Examples of suitable transdermal devices are described, for instance, in U.S. Pat. No. 4,818, 540 issued Apr. 4, 1989 to Chinen, et al., herein incorporated by reference.

Compositions of the peptide agents suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection of the peptide agents.

Compositions of the peptide agents suitable for transbronchial and transalveolar administration include, but not limited to, various types of aerosols for inhalation. For instance, pentamidine is administered intranasally via aerosol to AIDS patients to prevent pneumonia caused by *pneumocystis carinii*. Devices suitable for transbronchial and transalveolar administration of the peptides are also embodiments. Such devices include, but are not limited to, atomizers and vaporizers. Many forms of currently available atomizers and vaporizers can be readily adapted to deliver peptide agents.

Compositions of the peptide agents suitable for gastrointestinal administration include, but not limited to, pharmaceutically acceptable powders, pills or liquids for ingestion and suppositories for rectal administration. Due to the most common routes of HIV infection and the ease of use, gastrointestinal administration, particularly oral, is the preferred embodiment of the present invention. Five-hundred milligram capsules having a tripeptide (GPG-$NH_2$) have been prepared and were found to be stable for a minimum of 12 months when stored at 4° C. As previously shown in other virus-host systems, specific antiviral activity of small peptides can be detected in serum after oral administration. (Miller et al., *Appl. Microbiol.,* 16:1489 (1968)). Since small peptides apparently evade degradation by the patient's digestive system, they are ideal for oral administration.

The peptide agents are also suitable for use in situations where prevention of HIV infection is important. For instances, medical personnel are constantly exposed to patients who may be HIV positive and whose secretions and body fluids contain the HIV virus. Further, the peptide agents can be formulated into antiviral compositions for use during sexual intercourse so as to prevent transmission of HIV. Such compositions are known in the art and also described in international application published under the PCT publication number WO90/04390 on May 3, 1990 to Modak et al., which is incorporated herein by referencein its entirety.

Aspects of the invention also include a coating for medical equipment such as gloves, sheets, and work surfaces that protects against HIV transmission. Alternatively, the peptide agents can be impregnated into a polymeric medical device. Particularly preferred are coatings for medical gloves and condoms. Coatings suitable for use in medical devices can be provided by a powder containing the peptides or by polymeric coating into which the peptide agents are suspended. Suitable polymeric materials for coatings or devices are those that are physiologically acceptable and through which a therapeutically effective amount of the peptide agent can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al. that is incorporated herein by reference in its entirety.

In the disclosure below, several toxicological studies on small peptides are provided and approaches to test the toxicity of other peptide agents are disclosed.

Small Peptide Toxicology Studies

Several toxicology studies on GPG-$NH_2$ have been performed and these assays can be reproduced using many more peptides (e.g., GKG-$NH_2$, CQG-$NH_2$, RQG-$NH_2$, KQG-$NH_2$, ALG-$NH_2$, GVG-$NH_2$, VGG-$NH_2$, ASG-$NH_2$, SLG-$NH_2$, and SPT-$NH_2$). (See e.g., U.S. Pat. No. 5,627,035 to Vahlne et al.). The effects of GPG-$NH_2$ on cultured lymphocytes is provided in the following example.

EXAMPLE 5

In this example, several toxicology studies that addressed the effects of small peptides on cultured lymphocytes are presented. Generally, none of the peptides used in the virus inhibition assays for HIV-1 tested at concentrations up to 2 mM exhibited any toxic effect on the cells used, as determined by their morphological appearance, trypan blue staining and cell growth. The toxicity of GPG-$NH_2$ was further tested in (i) a plaque reduction assay and (ii) a yield inhibition assay of HSV-1. GPG-$NH_2$ failed to reduce HSV-1 replication at concentrations up to 1 mM that not only confirmed its lack of toxicity but also demonstrated that the small peptide selectively inhibits HIV-related viruses. This view was reinforced by the observation that GPG-$NH_2$ also failed inhibit either influenza or polio viruses.

Next, the toxicity to normal human lymphomonocytic cells (PBMC) was examined. At does as high as 2 mM and exposure as long as 4 days, GPG-$NH_2$ did not appreciably affect the viability of cultured monocytes and lymphocytes. The effect of GPG-$NH_2$ on in vitro proliferative response of human mononuclear cells was also tested. GPG-$NH_2$ exerted marginal if any direct anti-proliferative properties on T cells and did not affect the function of accessory cells (e.g. monocytes and dendritic cells) at a dose of 20 $\mu$M.

The in vitro 50% cytotoxic concentrations ($CC_{50}$) of various cell lines was also assessed. Accordingly, different concentrations of GPG-$NH_2$, up to 40 mM, was supplemented into the medium culture of T-cell lines $HUT_{78}$, H9, CEM-SS, MT-2 and (non) induced ACH-2, as well as, the macrophage derived cell lines Jurkat-tat III, THP-1 and (non) induced U-1 cells. After 3 days of incubation, the number of cells were counted. Trypan-blue dye exclusion and cell counting of HUT78, MT-2 and Jurkat-tat III showed about a 40% inhibition of cell growth for 3 days of culture in the presence of 40 mM GPG-NH2. H9, CEM-SS, and THP-1 showed a less than 20% decrease in cell number at this GPG-NH2 concentration. Therefore, the ratio of $CC_{50}/IC_{50}$ in vitro is $>10^4$. The toxicology experiments presented above prove that small peptides are of low toxicity to lymphocytes even at high concentrations.

The effects of large doses of small peptide on rodents was also analyzed and these experiments are presented in the next example.

EXAMPLE 6

In this example, the results from several in vivo toxicology studies on small peptides administered in large doses to rodents are presented. In a first experiment, a large single dose of small peptide was delivered to mice and the toxic effects were analyzed. An intravenous injection of GPG-$NH_2$ in the tail vein of adult mice at concentrations of up to 1 g per kilo bodyweight gave no apparent toxic effects to the animals. In a second experiment, several doses of varying amounts of a small peptide were delivered to mice for almost three weeks. Groups of mice (five mice in each group) were given intraperitoneal injections of GPG-$NH_2$ (0.01, 0.1 and 1 g per kilo bodyweight and day, respectively) starting at an age of 6 days. Daily injections were continued for 18 days. Compared to controls, there was no significant influence of GPG-$NH_2$ on the mice. In a similar experiment, a four week toxicology study of GPG-$NH_2$ was performed by Scantox A/S in Denmark. GPG-$NH_2$ was given orally to rats at doses up to 1 g per kilo bodyweight per day for twenty eight days. No signs of toxicity to the animals was observed. These in vivo toxicology experiments prove that the small peptides described herein are of low toxicity to mammals and can be safely provided at large doses.

In further studies, the stability of small peptides in human blood and plasma was analyzed. The example below discloses these experiments.

EXAMPLE 7

This example describes several studies that were performed to access the stability of small peptides in human blood and plasma. Accordingly, human blood was taken freshly and treated with EDTA. Plasma was separated by centrifuging at 2,500 rpm for 20 minutes. GPG-NH$_2$ was added into blood or plasma at concentrations of 10 mM or 50 mM followed by incubation in 37° C. for 1, 2 and 4 hours, respectively. As a control, GPG-NH$_2$ was added into RPMI 1640 medium supplemented with 10% (v/v) heat-inactivated fetal bovine serum (FBS, GIBCO), penicillin (100 u/ml), streptomycin (100 u/ml) and Polybrene (Sigma, 2 µg/ml) and incubated in the same way. After incubation in 37° C., the GPG-NH$_2$ containing blood was centrifuged at 2,500 rpm for 20 minutes to isolate plasma. Some of the plasma samples were treated with CaCl$_2$ at concentration of 5 mM in 37° C. for 10 minutes followed by centrifuging at 13,000 rpm for 30 minutes and the supernatant are referred to as CaCl$_2$ treated plasma. Then all the GPG-NH$_2$ containing plasma samples were diluted in RPMI medium to give the final concentrations 20 µM or 100 µM of GPG-NH$_2$ (500 fold dilutions) and were then used in HIV-1 replication assays.

The replication assays were performed on HUT$_{78}$ cells and the HIV-1 SF-2 virus strain was used. Briefly, approximately 200,000 cells were resuspended in the diluted GPG-amide containing medium, plasma, or plasma from blood. The GPG-NH$_2$ containing medium, plasma, or plasma from blood was incubated with the cells for either 1 hr, 2 hr, or 4 hr at 37° C. Subsequently, SF-2 virus was added at 25 TCID$_{50}$. After adsorption of 1 hour, cells were washed three times in RPMI medium then resuspended in the proper GPG-amide containing plasma and incubated at 37° C. in 5% CO$_2$ with humidity. Culture supernatants were collected every four days and medium was changed until day 14 post infection. To monitor the replication of virus, HIV-1 p24 antigen protein in the supernatants was assayed using a commercially available kit (Abbott). The HIV-1 p24 assay was performed on the supernatants from day 7 and day 14 post infection. No significant difference in the ability to inhibit HIV-1 with GPG-NH$_2$ supplemented medium, plasma, or plasma from blood was observed.

Figure 7:
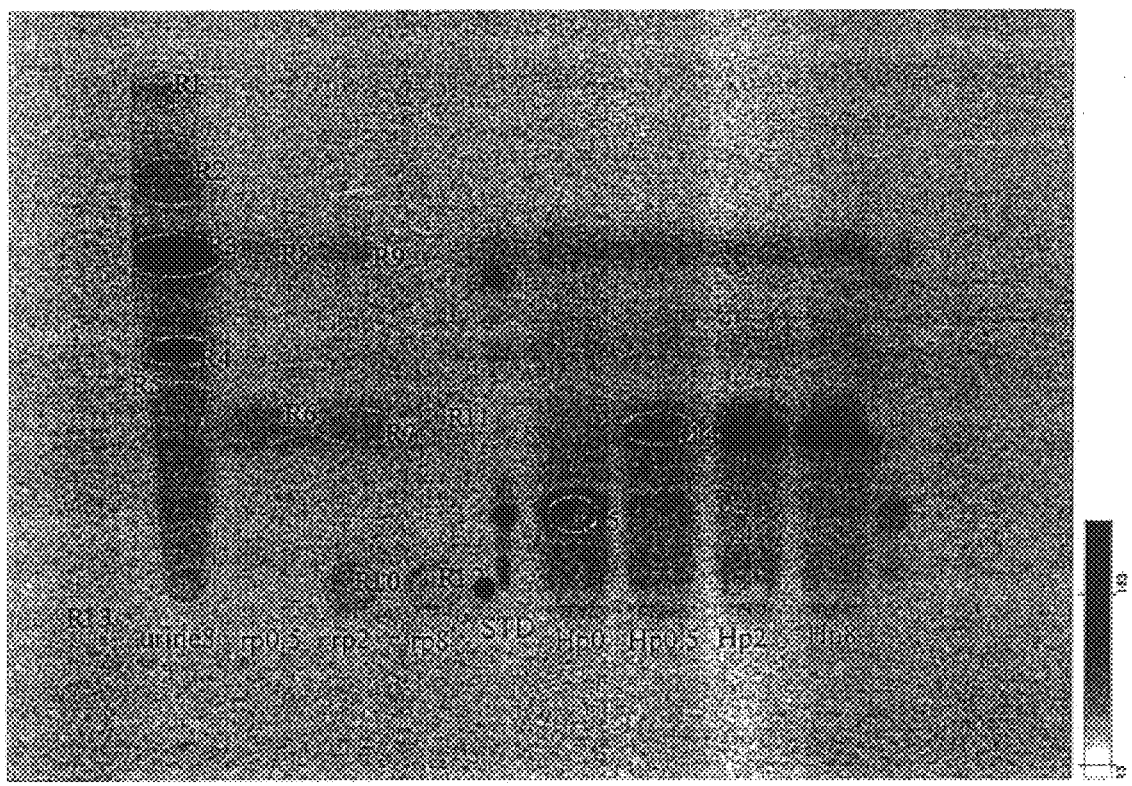
FIG. 7 illustrates a thin layer chromatography support having separated thereon non-protein bound radioactive labeled compounds from rat urine and rat plasma (rp) sampled after oral feeding of $^{14}$C-GPG-NH$_2$, as well as human plasma (Hp) incubated with $^{14}$C-GPG-NH$_2$; the sampling times are suffixed and R1–R13 serve to indicate the position of identified radioactive compounds.

The stability of GPG-NH$_2$ in human plasma was also assessed chemically by thin layer chromatography (TLC). (See FIG. 7). In this experiment, $^{14}$C GPG-NH2 was incubated with human plasma at 37° C. for 30 minutes, two hours, or eight hours and then the proteins were separated by TLC and were visualized by exposure of the chromatograph to autoradiography film. As shown in FIG. 7 (lanes Hp0, Hp0.5, Hp2, and Hp8), a slight shift in mobility of the small peptide was observed. Although the mobility of the small peptide increased somewhat after 30 minutes of incubation in the human plasma at 37° C., no further change in mobility was observed at up to 8 hours. Mass-spectrometry analysis (electrospray analysis) of the TLC spots verified that all spots, including the spot with increased mobility, were GPG-NH$_2$. The experiments above prove that the small peptides described herein are stable in human blood and plasma; they retain their antiviral properties, and are not degraded by plasma proteinases.

In the disclosure below, several studies on the adsorption, distribution, and metabolism of the small peptides are provided.

Adsorption, Distribution, and Metabolism of Small Peptides

Figure 8:
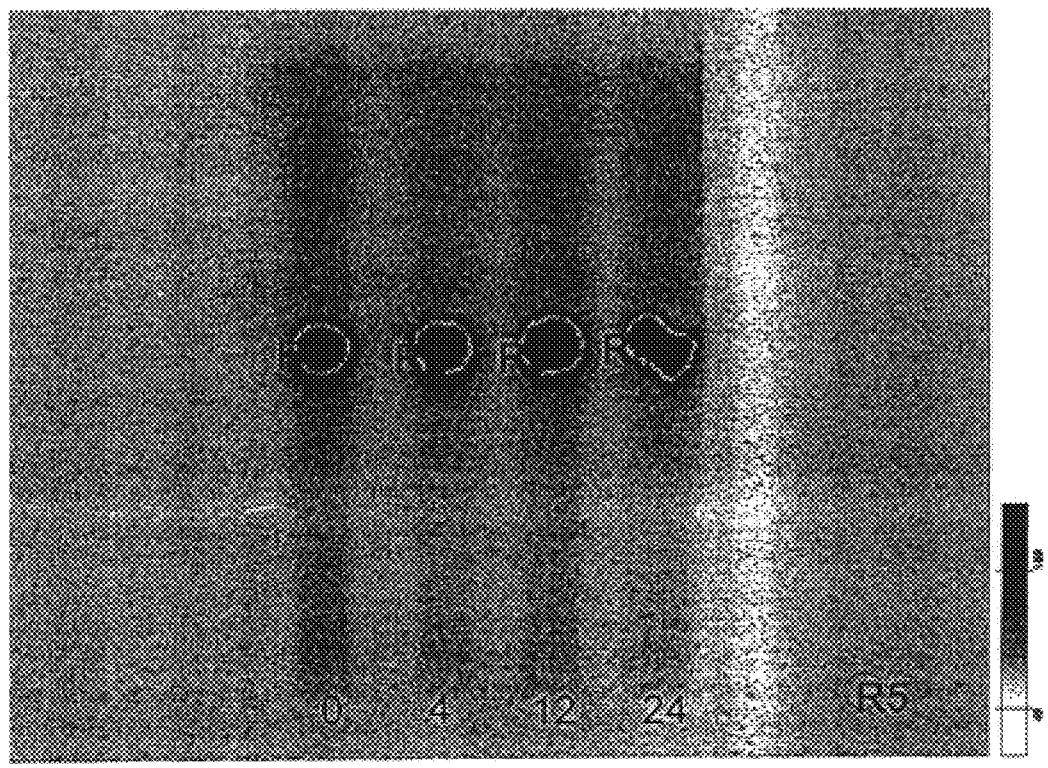
FIG. 8 is a thin layer chromatography support having separated thereon $^{14}$C-GPG-NH$_2$ that was treated with 0.1N HCl and 50 mM KCl and sampled over a 24 hour period; the numbers represent the time of acid exposure and the R serves to indicate the position of the identified $^{14}$C-GPG-NH$_2$.

Because an oral administration of a pharmaceutical comprising a small peptide is desired, the acid stability of small peptides was assessed by incubating $^{14}$C-labelled GPG-NH$_2$ in a solution of 50 mM KCl and 0.1M HCl for various time periods. After acid hydrolysis, the radiolabeled tripeptide was analyzed by thin layer chromatography (TLC) and the HPTLC plate was developed with 25% methanol: 25% isopropanol: 15% butanol: 35% (0.1N HOAc and 0.1N NaOAc). As can be seen in FIG. 8, incubation of the tripeptide for up to 24 hours did not affect the mobility, and hence not the molecular structure, of the GPG-NH$_2$. This result established that small peptides survive acidic conditions similar to that found in the stomach.

Additionally, the in vitro uptake of small peptides from the culture medium into the cells was studied in a series of experiments. Accordingly, HUT$_{78}$, Jurkat-tat III, and MT-2 cells were incubated with $^{14}$C-labelled GPG-NH$_2$ 165 nCi (equivalent to 0.7 µM of GPG-NH$_2$). An uptake of the small peptide was observed and between 8% (Jurkat-tat III cells) and 20% (HUT$_{78}$ cells) of the GPG-NH$_2$ was incorporated in the cells. This result proved that the incorporation of small peptides into several cell types was effective.

Further, the in vivo uptake of small peptides was analyzed in rats. Rats were fed $^{14}$C GPG-NH$_2$ and, after various time points, blood, urine, and tissue samples were collected from the animals. Samples of rat urine taken eight hours after feeding and rat plasma taken 30 minutes, two hours, and eight hours after feeding were separated on a TLC plate, as shown in FIG. 7 (designated urine8, rp0.5, rp2, and rp8, accordingly). All the tissues were kept in -20° C. after necropsy before any assay was performed. Ten to thirty micrograms of the tissue samples were collected from three different locations of each organ analyzed and the organ tissue was subsequently dissolved in 250 µl of tissue solublizer (OptiSolv, LKB-Wallac) at 45° C. for four to six hours. The homogenized tissue solutions were decolorized by the addition of 50 µl of 30% H$_2$O$_2$ and 100 µl of isopropanol before 3 ml of 0.05M HCl acidified scintillation cocktail (Luma Gel, Lumac/3M) was added. The radioactivity was determined with a beta scintillation counter (LKB-Wallac 1218 Rack Beta). The free/unbound GPG-NH$_2$ in the plasma was collected by precipitation with one part of plasma and two parts of ethanol followed by incubation at -70° C. for one hour and centrifugation at 20,000×g for 15 min at 4° C. Blood cell samples were diluted with PBS (in the ratio of 2 parts of blood cells to 1 part of PBS) before 10 µl of the mixture was sampled and analyzed as the tissue samples. Five to 20 µl of plasma and urine samples were directly mixed with 3 ml of Ready Safe (Beckman) fluid before quantification. The results giving the distribution and the basis for calculation of maximum uptake are shown in Tables 10 and 11. The values are expressed in nCi.

TABLE 11

| Animal number* nCi/ml or g tissue | 1 | 2 | 3 | 4 | 5 | avg |
|---|---|---|---|---|---|---|
| Brain | 48 | 34 | 31 | 30. | 33 | 35 |
| Kidneys | 450 | 491 | 467 | 446 | 477 | 466 |
| Liver | 599 | 413 | 454 | 507 | 503 | 495 |
| Spleen | 383 | 428 | 414 | 195 | 413 | 366 |
| Thymus | 366 | 288 | 290 | 338 | 372 | 331 |
| Blood cells | 90 | 81 | 99 | 95 | 101 | 93 |
| Plasma | 140 | 126 | 121 | 142 | 124 | 130 |

TABLE 11-continued

| Animal number* nCi/ml or g tissue | 1 | 2 | 3 | 4 | 5 | avg |
|---|---|---|---|---|---|---|
| Urine | 5,846 | 5,068 | 6,841 | 4,557 | 5,986 | 5,660 |
| Total urine | 7,016 | 7,096 | 3,284 | 283 | 2,395 | 4,015 |

*Animals were sacrificed after 4 hours.

TABLE 12

| Animal number* | 6 | 7 | 8 | 9 | 10 | avg |
|---|---|---|---|---|---|---|
| Brain | 43 | 27 | 28 | 25 | 29 | 30 |
| Kidneys | 255 | 488 | 461 | 401 | 468 | 415 |
| Liver | 537 | 419 | 478 | 458 | 578 | 494 |
| Spleen | 307 | 281 | 257 | 336 | 285 | 293 |
| Thymus | 340 | 350 | 323 | 349 | 311 | 334 |
| Blood cells | 51 | 72 | 87 | 71 | 108 | 78 |
| Plasma | 138 | 123 | 135 | 129 | 148 | 135 |
| Urine | 2,992 | 5,040 | 3,121 | 4,297 | 2,175 | 3,525 |
| Total urine | 6,463 | 6,653 | 11,173 | 10,227 | 7,613 | 8,426 |

*Animals sacrificed after 8 hours.

The calculation of the maximum uptake was determined as follows. The total feeding was 800 $\mu$Ci/kg rat body weight (160 $\mu$Ci in total per animal). On the assumption that the GPG-NH$_2$ and its metabolities were evenly distributed in the body, the GPG-NH$_2$ present in tissues would be the average counts/g from different tissues from the total number of animals studied divided by the total number of animals and multiplied by the body weight and the factor 0.9. This factor is derived to omit the blood volume since an estimate of blood volume is roughly 10% of the average body weight. For example (from the data of animals 1–5), if the total body weight for five rats was 207 g and the radioactivity detected from various tissues was (35+466+495+366+331) or 1,693 nCi and the radioactivity detected from blood was (93+130) or 223 nCi and the radioactivity detected in urine was 4, 015 nCi, the maximal intake of the small peptide can be calculated as:

tissue: (35+466+495+366+331)/5*207*0.9=63,240 nCi fluids: blood (93+130)*207*0.1=4,642 nCi urine: 4,015 nCi Sum: (63.24+4.642+4.015)/800*0.207=0.4342, or 43% maximal uptake The relative distribution of retained/immobilized GPG-NH$_2$ and its metabolites in sampled tissues was observed to be highest in the liver followed by the kidney, followed by the spleen, followed by the thymus, followed by the brain. The radioactivity in the urine was observed to double between hours 4 and 8. Mass spectrometric data (electrospray mass spectrometry) of the urine radioactive spot from the TLC plate showed that only a small portion of the radioactivity in urine was intact GPG-NH$_2$. (See FIG. 7). The results from the in vivo studies above proved that a significant amount of small peptides are effectively delivered to blood, plasma, and several different tissues.

Figure 9:
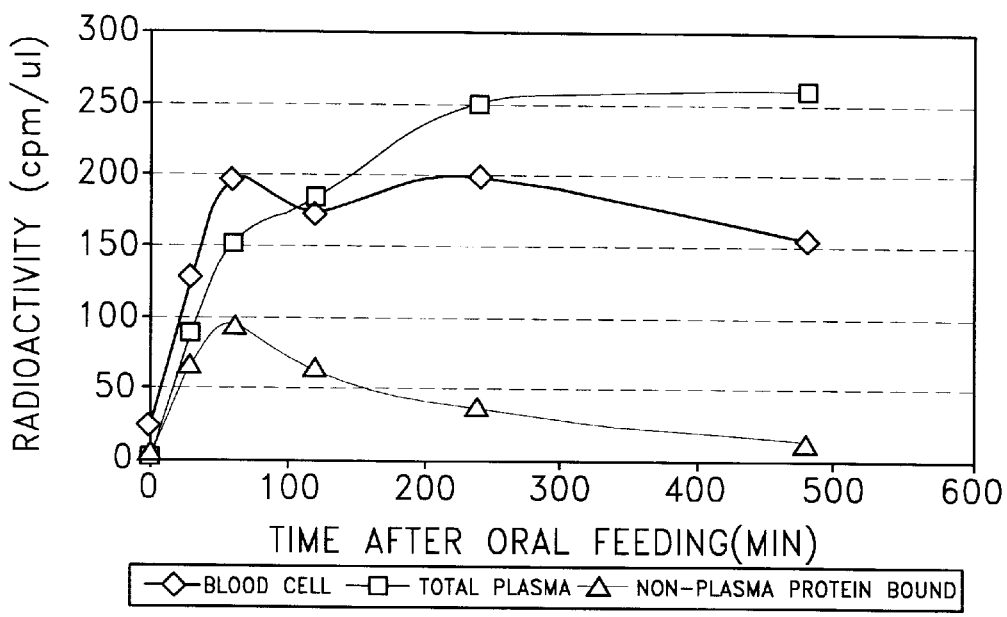
FIG. 9 is a graph of the partition of $^{14}$C-GPG-NH$_2$ and its metabolites in rat blood.
Figure 10:
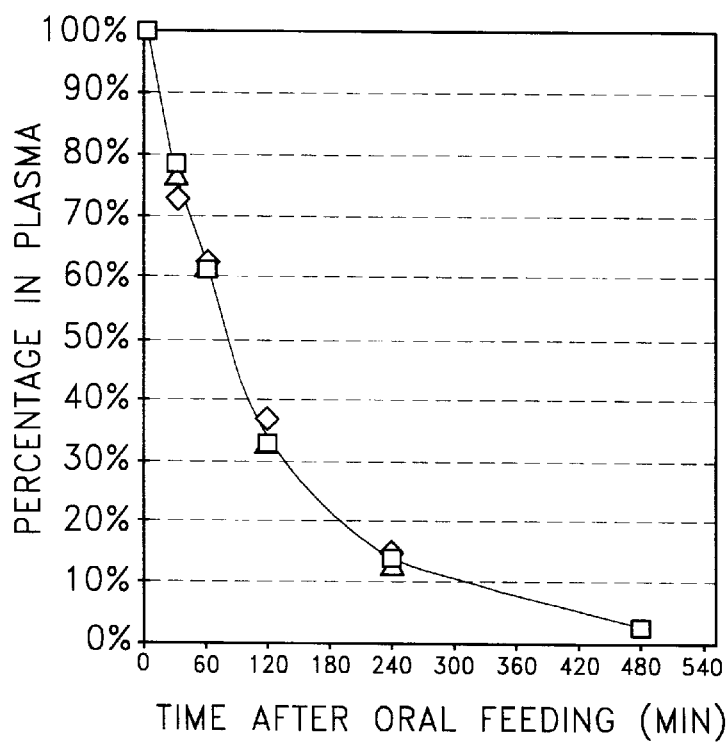
FIG. 10 is a graph of the elimination of radioactivity from the plasma fraction of rats that were orally fed $^{14}$C-GPG-NH$_2$.

Additionally, as shown in FIGS. 9 and 10, a significant amount of small peptide remains in the plasma fraction over a long period of time. In FIG. 9, the distribution of radioactivity between blood cells, plasma protein bound, as well as, non protein bound (free) plasma radioactivity is shown. The elimination of radioactivity from the plasma fraction is depicted in FIG. 10. The tripeptide GPG-NH$_2$ has a half-life of 86.5 minutes. Protein bound radioactivity was assayed after precipitation with two parts of 99.5% ethanol. From the uptake and distribution data and the TLC data above, the minimal uptake of intact GPG-NH$_2$ recovered from the plasma was calculated and, in one hour after feeding of the rats, at least 1% of fed GPG-NH$_2$ could be recovered as protein free GPG-NH$_2$ in the plasma.

For the assessment of biologically active GPG-NH$_2$ in the plasma of animals fed the small peptide, plasma samples were prepared from blood obtained from the rats of the four week toxicology study the day after the last feeding. The plasma samples were diluted ⅕ in RPMI medium and were adminstered to PBMC infected with the SF162 strain of HIV-1, as described above. Viral infectivity was then monitored at seven, eleven, and fourteen days post infection by detecting the amount of p24 in the supernatent using a commercially available detection assay. (Abbott). As shown in Table 12, the sera obtained from the rats treated with the small peptide retained the ability to inhibit viral infectivity. In some cases, the administration of as little as 10 $\mu$M GPG-NH$_2$ provided a sufficient concentration of small peptide in the plasma to enable the inhibition of HIV-1 replication. The percent reduction was calculated as in Table 6. The results from these experiments established that small peptides described herein can be maintained at concentrations in the body of an animal that are effective at inhibiting HIV replication.

TABLE 13

| Animal #. | Feeding GPG (mg/ml) | p24 (pg/ml) | % reduction |
|---|---|---|---|
| Exp. 1 | | | |
| day 7 | | | |
| 14 | 0 | 543.0 | 0 |
| 34 | 10 | 93.3 | 82.8 |
| 53 | 30 | 24.0 | 95.6 |
| 73 | 100 | 174.7 | 67.8 |
| day 14 | | | |
| 14 | 0 | 22678 | 0 |
| 34 | 10 | 1636 | 92.8 |
| 53 | 30 | 938 | 95.9 |
| 73 | 100 | 9211 | 59.4 |
| Exp. 2 | | | |
| day 7 | | | |
| 16 | 0 | 321.8 | 0 |
| 36 | 10 | 219.2 | 31.9 |
| 56 | 30 | 194.3 | 39.6 |
| 76 | 100 | 173.5 | 46.1 |
| day 14 | | | |
| 16 | 0 | 4075.4 | 0 |
| 36 | 10 | 4760.8 | 0 |
| 56 | 30 | 3574.4 | 12.3 |
| 76 | 100 | 2203.7 | 45.9 |
| Exp. 3 | | | |
| day | | | |
| 18 | 0 | 183.9 | 0 |
| 38 | 10 | 255.6 | 0 |
| 58 | 30 | 107.3 | 41.7 |
| 78 | 100 | 96.9 | 47.3 |
| day 14 | | | |
| 18 | 0 | 7578.4 | 0 |
| 38 | 10 | 6700.6 | 11.6 |
| 58 | 30 | 6893.0 | 9.1 |
| 78 | 100 | 7578.4 | 0 |

TABLE 13-continued

| Animal #. | Feeding GPG (mg/ml) | p24 (pg/ml) | % reduction |
|---|---|---|---|
| Exp. 4 | | | |
| day 11 | | | |
| 13 | 0 | 242 | 0 |
| 33 | 10 | 170 | 29.8 |
| 52 | 30 | 487.4 | 0 |
| 71 | 100 | 51.7 | 78.6 |
| Exp. 5 | | | |
| day 7 | | | |
| 15 | 0 | 304.8 | 0 |
| 35 | 10 | 79.6 | 73.9 |
| 55 | 30 | 439.3 | 0 |
| 75 | 100 | 60 | 80.3 |

The proteins from whole plasma were also analyzed by column chromatography and fractionated and crude protein were separated by sodium dodecyl sulfate polyacrylamide gel (10%) electrophoresis (SDS/PAGE). Rat plasma samples were partially purified with size exclusion (Sepharose G-50, Phamacia) chromatography (0.4×6 cm), in a buffer of 10 mM Tris-HCl pH 8.3 and 50 mM KCl. Eluate was then separated by anionic exchange chromatography by using an increasing stepwise gradient of NaCl in a buffer of 10 mM Tris-HCl pH8.3 (Sepharose CL-6B DEAE, 0.4×6 cm). The eluate was monitored and pooled according to the radioactivity (Ready Safe, Beckman; LKB1218, Sweden). The protein fractions with strong signal were separated on a 10% SDS-PAGE and were subsequently blotted onto PVDF (polyvinylidene difluoride, BioRad) membrane before being subjected to Edman N-terminal amino acid sequencing (Applied Biosystems Procise Sequencer, USA).

Figure 11:
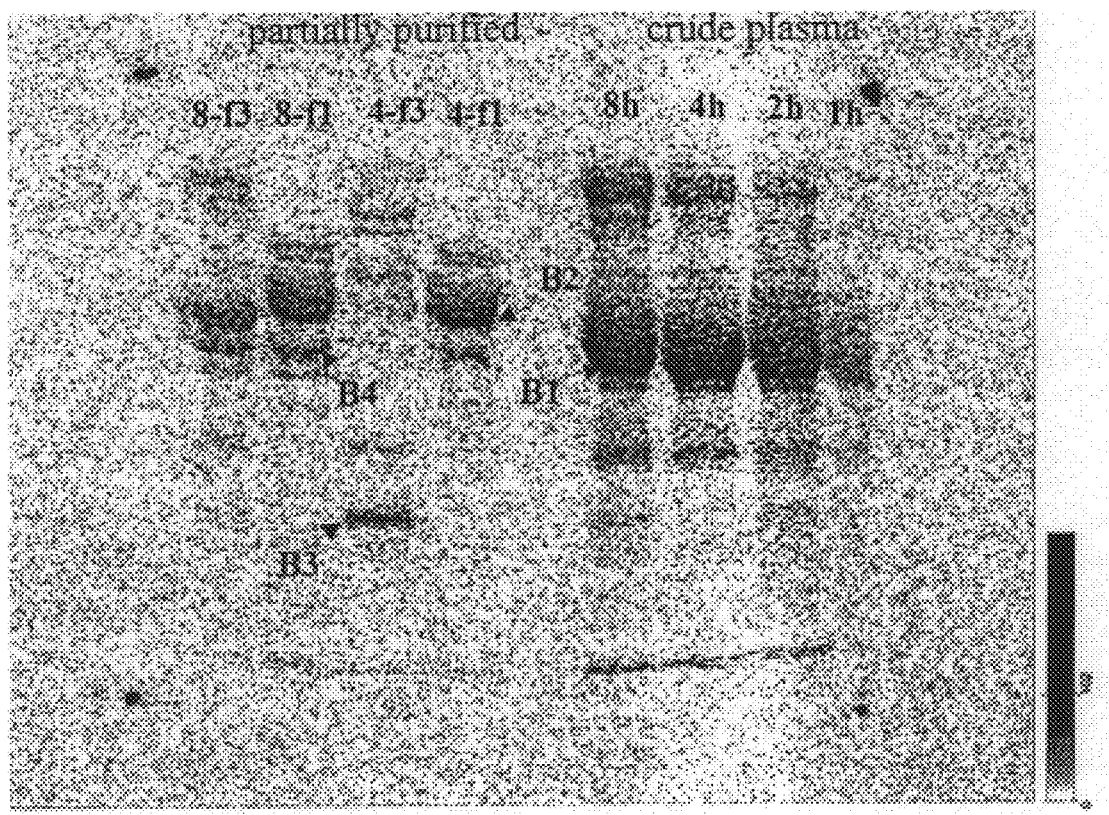
FIG. 11 shows crude and fractionated rat plasma proteins that were separated on a 10% SDS/PAGE; 8-f3 refers to the third fraction taken from a sample at 8 hours after administration of $^{14}$C-GPG-NH$_2$, 8-fl refers to the first fraction taken from a sample at 8 hours after administration of $^{14}$C-GPG-NH$_2$, 4-f3 refers to the third fraction taken from a sample at 4 hours after administration of $^{14}$C-GPG-NH$_2$, 4-f1 refers to the first fraction taken from a sample at 4 hours after administration of $^{14}$C-GPG-NH$_2$, 8 h, 4 h, 2 h, and 1 h refer to the time the sample was taken after administration of $^{14}$C-GPG-NH$_2$, and B1–B4 serve to indicate the position of identified proteins.

As shown FIG. 11, little radioactivity was observed to be covalently associated with proteins 60 minutes after feeding the animal. The proteins marked B1–B4 were sequenced and determined to be alpha-1 antitrypsin (B1), pentaxin (B-2), C-reactive protein (B-3), and B-4 could not be identified. These proteins are all synthesized in the liver. One interpretation is that hydrolyzed GPG-NH$_2$ was reutilized in the liver protein synthesis. These experiments established that small peptides are metabolized in the body and, since the identified associated protein (B-1, B-2, and B-3) are all synthesized in the liver, hydrolysis and reutilization of small peptides occured in the liver.

Although the invention has been described with reference to certain embodiments and examples, it should be understood that various modifications can be made without departing from the spirit of the invention. Accordingly, the invention is limited only by the following claims.

What is claimed is:

1. A peptide selected from the group consisting of Gly-Lys-Gly-NH$_2$, Arg-Gln-Gly-NH$_2$, Cys-Gln-Gly-NH$_2$, Lys-Gln-Gly-NH$_2$, Ala-Leu-Gly-NH$_2$, Gly-Val-Gly-NH$_2$, Val-Gly-Gly-NH$_2$, Ala-Ser-Gly-NH$_2$, Ser-Leu-Gly-NH$_2$, and Ser-Pro-Thr-NH$_2$.

2. The peptide of claim 1, wherein the peptide is Gly-Lys-Gly-NH$_2$.

3. The peptide of claim 1, wherein the peptide is Arg-Gln-Gly-NH$_2$.

4. The peptide of claim 1, wherein the peptide is Cys-Gln-Gly-NH$_2$.

5. The peptide of claim 1, wherein the peptide is Lys-Gln-Gly-NH$_2$.

6. The peptide of claim 1, wherein the peptide is Ala-Leu-Gly-NH$_2$.

7. The peptide of claim 1, wherein the peptide is Ser-Leu-Gly-NH$_2$.

8. The peptide of claim 1, wherein the peptide is Gly-Val-Gly-NH$_2$.

9. The peptide of claim 1, wherein the peptide is Val-Gly-Gly-NH$_2$.

10. The peptide of claim 1, wherein the peptide is Ala-Ser-Gly-NH$_2$.

11. The peptide of claim 1, wherein the peptide is Ser-Pro-Thr-$NH_2$.

12. The peptide of claim 1, further comprising a pharmaceutically acceptable carrier.

13. The peptide of claim 1, further comprising a support.

14. The peptide of claim 2, further comprising a pharmaceutically acceptable carrier.

15. The peptide of claim 2, further comprising a support.

16. The peptide of claim 3, further comprising a pharmaceutically acceptable carrier.

17. The peptide of claim 3, further comprising a support.

18. The peptide of claim 4, further comprising a pharmaceutically acceptable carrier.

19. The peptide of claim 4, further comprising a support.

20. The peptide of claim 5, further comprising a pharmaceutically acceptable carrier.

21. The peptide of claim 5, further comprising a support.

22. The peptide of claim 6, further comprising a pharmaceutically acceptable carrier.

23. The peptide of claim 6, further comprising a support.

24. The peptide of claim 7, further comprising a pharmaceutically acceptable carrier.

25. The peptide of claim 7, further comprising a support.

26. The peptide of claim 8, further comprising a pharmaceutically acceptable carrier.

27. The peptide of claim 8, further comprising a support.

28. The peptide of claim 9, further comprising a pharmaceutically acceptable carrier.

29. The peptide of claim 9, further comprising a support.

30. The peptide of claim 10, further comprising a pharmaceutically acceptable carrier.

31. The peptide of claim 10, further comprising a support.

32. The peptide of claim 11, further comprising a pharmaceutically acceptable carrier.

33. The peptide of claim 11, further comprising a support.

* * * * *